United States Patent
Torrens-Jover et al.

(10) Patent No.: US 10,640,468 B2
(45) Date of Patent: May 5, 2020

(54) 1-(4-(2-((1-(3,4-DIFLUOROPHENYL)-1H-PYRAZOL-3-YL)METHOXY)ETHYL)PIPERAZIN-1-YL)ETHANONE SALTS

(71) Applicant: ESTEVE PHARMACEUTICALS S.A., Barcelona (ES)

(72) Inventors: Antoni Torrens-Jover, Barcelona (ES); Carmen Almansa-Rosales, Barcelona (ES)

(73) Assignee: ESTEVE PHARMACEUTICALS, S.A., Torre Esteve Passeig de la Zona Franca, Barcelona (ES)

( * ) Notice: Subject to any disclaimer, the term of this patent is extended or adjusted under 35 U.S.C. 154(b) by 0 days.

(21) Appl. No.: 15/757,177

(22) PCT Filed: Sep. 1, 2016

(86) PCT No.: PCT/EP2016/070604
§ 371 (c)(1),
(2) Date: Mar. 2, 2018

(87) PCT Pub. No.: WO2017/037166
PCT Pub. Date: Mar. 9, 2017

(65) Prior Publication Data
US 2018/0251430 A1 Sep. 6, 2018

(30) Foreign Application Priority Data
Sep. 2, 2015 (EP) .................... 15382436

(51) Int. Cl.
*C07D 403/12* (2006.01)
*C07D 231/12* (2006.01)

(52) U.S. Cl.
CPC ......... *C07D 231/12* (2013.01); *C07D 403/12* (2013.01); *C07B 2200/13* (2013.01)

(58) Field of Classification Search
CPC ........................... C07D 403/12; C07D 231/12
See application file for complete search history.

(56) References Cited

U.S. PATENT DOCUMENTS

2017/0273948 A1* 9/2017 Vela Hern Ndez .......... A61K 31/415

FOREIGN PATENT DOCUMENTS

WO 2011147910 A1 12/2011

OTHER PUBLICATIONS

Berge et al. J. Pharmaceutical Salts, vol. 66(1), pp. 1-19 (1977) (Year: 1977).*
International Search Report and Written Opinion issued by the International Searching Authority in International Application No. PCT/EP2016/070604, dated Oct. 12, 2016.
Anderson, "Chapter 11, Tools for Purifying the Product: Column Chromatography, Crystallization and Reslurrying", Practical Process Research and Development, Academic Press, San Diego, 2000, pp. 223-247.
Bastin et al., "Salt Selection and Optimisation Procedures for Pharmaceutical New Chemical Entities", Organic Process Research And Development, vol. 4, No. 5, Jul. 19, 2000, pp. 427-435.
Hilfiker et al. "Chapter 1, Relevance of Solid-state Properties for Pharmaceutical Products", Polymorphism in the Pharmaceutical Industry, 2006, Wiley-VCH, pp. 1-19.
Weinheim, "Tables of Salt-Forming Acids and Bases", Handbook of Pharmaceutical Salts—Properties, Selection, and Use, Jan. 1, 2002, Verlag Helvetica Chimica Acta; Wiley-VCH, Zurich, pp. 331-345.

* cited by examiner

*Primary Examiner* — Sun Jae Yoo
(74) *Attorney, Agent, or Firm* — Hueschen and Sage

(57) ABSTRACT

The present invention relates to 1-(4-(2-((1-(3,4-difluorophenyl)-1H-pyrazol-3-yl)methoxy)ethy)piperazin-1-y)ethanone salts, specifically to the hydrochloride and to the maleate, to pharmaceutical compositions comprising them, and to their use in therapy and/or prophylaxis of sigma receptor associated diseases.

5 Claims, 25 Drawing Sheets

1-(4-(2-((1-(3,4-DIFLUOROPHENYL)-1H-PYRAZOL-3-YL)METHOXY)ETHYL)PIPERAZIN-1-YL)ETHANONE SALTS

CROSS-REFERENCE TO RELATED APPLICATIONS

This application is a U.S. National Stage of International Patent Application No. PCT/EP2016/070604 filed Sep. 1, 2016, which claims the benefit of European Patent Application No. 15382436.2 filed Sep. 2, 2015, both of which applications are herein incorporated by reference in their entireties.

FIELD OF THE INVENTION

The present invention relates to 1-(4-(2-((1-(3,4-difluorophenyl)-1H-pyrazol-3-yl)methoxy)ethyl)piperazin-1-yl)ethanone salts, specifically to the hydrogen halides salts and simple carboxylic diacid salts, to pharmaceutical compositions comprising them, and to their use in therapy and/or prophylaxis of sigma receptor associated diseases.

BACKGROUND

The search for new therapeutic agents has been greatly aided in recent years by better understanding of the structure of proteins and other biomolecules associated with target diseases. One important class of these proteins is the sigma (σ) receptor, a cell surface receptor of the central nervous system (CNS) which may be related to the dysphoric, hallucinogenic and cardiac stimulant effects of opioids. From studies of the biology and function of sigma receptors, evidence has been presented that sigma receptor ligands may be useful in the treatment of psychosis and movement disorders such as dystonia and tardive dyskinesia, and motor disturbances associated with Huntington's chorea or Tourette's syndrome and in Parkinson's disease (Walker, J. M. et al, *Pharmacological Reviews*, 1990, 42, 355). It has been reported that the known sigma receptor ligand rimcazole clinically shows effects in the treatment of psychosis (Snyder, S. H., Largent, B. L. J. Neuropsychiatry 1989, 1, 7). The sigma binding sites have preferential affinity for the dextrorotatory isomers of certain opiate benzomorphans, such as (+)-SKF 10047, (+)-cyclazocine, and (+)-pentazocine and also for some narcoleptics such as haloperidol.

The sigma receptor has at least two subtypes, which may be discriminated by stereoselective isomers of these pharmacoactive drugs. SKF 10047 has nanomolar affinity for the sigma-1 ($\sigma_1$) receptor and has micromolar affinity for the sigma-2 ($\sigma_2$) isoform. Haloperidol has similar affinities for both subtypes. Endogenous sigma ligands are not known, although progesterone has been suggested to be one of them. Possible sigma-site-mediated drug effects include modulation of glutamate receptor function, neurotransmitter response, neuroprotection, behavior, and cognition (Quirion, R. et al. *Trends Pharmacol. Sci.*, 1992, 13:85-86). Most studies have implied that sigma binding sites (receptors) are plasmalemmal elements of the signal transduction cascade. Drugs reported to be selective sigma ligands have been evaluated as antipsychotics (Hanner, M. et al. *Proc. Natl. Acad. Sci.*, 1996, 93:8072-8077). The existence of sigma receptors in the CNS, immune and endocrine systems have suggested a likelihood that it may serve as link between the three systems.

In view of the potential therapeutic applications of agonists or antagonists of the sigma receptor, a great effort has been directed to find selective ligands. Thus, the prior art discloses different sigma receptor ligands. 1-(4-(2-((1-(3,4-difluorophenyl)-1H-pyrazol-3-yl)methoxy)ethyl)piperazin-1-yl)ethanone is one of such promising sigma receptor ligands. The compound and its synthesis are disclosed and claimed in WO 2011/147910.

1-(4-(2-((1-(3,4-Difluorophenyl)-1H-pyrazol-3-yl)methoxy)ethyl)piperazin-1-yl)ethanone is a highly selective sigma-1 ($\sigma_1$) receptor antagonist. It displays strong analgesic activity in the treatment and prevention of chronic and acute pain, and particularly, neuropathic pain. The compound has a molecular weight of 364.39 Da and a pKa of 6.37. The structural formula of the compound is:

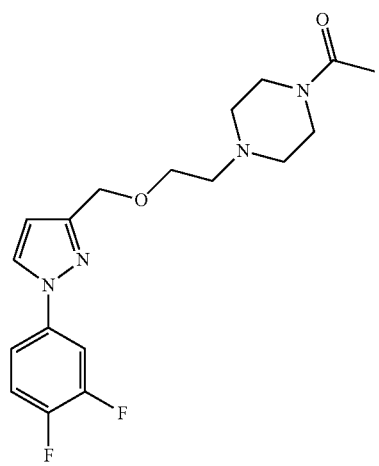 [SMILES: CC(=O)N1CCN(CCOCc2ccn(-c3ccc(F)c(F)c3)n2)CC1]

To carry out its pharmaceutical development and realize its potential, there is a need in the art for additional forms of 1-(4-(2-((1-(3,4-difluorophenyl)-1H-pyrazol-3-yl)methoxy)ethyl)piperazin-1-yl)ethanone that will facilitate the preparation of better formulations of this active pharmaceutical ingredient.

In this regard, alternative forms of the compound may have widely different properties such as, for example, enhanced thermodynamic stability, higher purity or improved bioavailability (e.g. better absorption, dissolution patterns). Specific compound forms could also facilitate the manufacturing (e.g. enhanced flowability), handling and storage (e.g. non-hygroscopic, long shelf life) of the compound formulations or allow the use of a lower dose of the therapeutic agent, thus decreasing its potential side effects. Thus, it is important to provide such forms, having improved properties for pharmaceutical use.

BRIEF DESCRIPTION OF THE INVENTION

In the present invention, after an extensive research on different forms of 1-(4-(2-((1-(3,4-difluorophenyl)-1H-pyrazol-3-yl)methoxy)ethyl)piperazin-1-yl)ethanone, it is surprisingly found and demonstrated that some of its crystalline salts and specifically the hydrogen halides salts and simple carboxylic diacid salts provides advantageous production, handling, storage and/or therapeutic properties.

Thus, in a first aspect the present invention relates to a 1-(4-(2-((1-(3,4-difluorophenyl)-1H-pyrazol-3-yl)methoxy)ethyl)piperazin-1-yl)ethanone crystalline salt selected from the group consisting of inorganic acids, sulphonic acids and organic acids.

In a preferred embodiment the 1-(4-(2-((1-(3,4-difluorophenyl)-1H-pyrazol-3-yl)methoxy)ethyl)piperazin-1-yl)

ethanone crystalline salt is selected from the group consisting of hydrochloric acid and hydrobromic acid.

In another preferred embodiment the 1-(4-(2-((1-(3,4-difluorophenyl)-1H-pyrazol-3-yl)methoxy)ethyl)piperazin-1-yl)ethanone crystalline salt is selected from the group consisting of maleic acid, fumaric acid, oxalic acid, malonic acid and succinic acid.

In a more preferred embodiment the 1-(4-(2-((1-(3,4-difluorophenyl)-1H-pyrazol-3-yl)methoxy)ethyl)piperazin-1-yl)ethanone crystalline salt is selected from the group consisting of hydrochloride, maleate, fumarate, malonate, succinate, oxalate and/or hydrobromide.

In a still more preferred embodiment the 1-(4-(2-((1-(3,4-difluorophenyl)-1H-pyrazol-3-yl)methoxy)ethyl)piperazin-1-yl)ethanone crystalline salt is selected from hydrochloride and/or maleate.

A further aspect of the present invention includes pharmaceutical compositions comprising a 1-(4-(2-((1-(3,4-difluorophenyl)-1H-pyrazol-3-yl)methoxy)ethyl)piperazin-1-yl)ethanone crystalline salt and at least a pharmaceutically acceptable carrier, adjuvant or vehicle.

In a further aspect the invention is directed to 1-(4-(2-((1-(3,4-difluorophenyl)-1H-pyrazol-3-yl)methoxy)ethyl)piperazin-1-yl)ethanone crystalline salt for use as medicament, preferably as sigma ligand, i.e., for use in the treatment and/or prophylaxis of a sigma receptor mediated disease or condition.

Another aspect of this invention relates to a method of treating and/or preventing a sigma receptor mediated disease which method comprises administering to a patient in need of such a treatment a therapeutically effective amount of a compound as above defined or a pharmaceutical composition thereof.

These aspects and preferred embodiments thereof are additionally also defined in the claims.

DETAILED DESCRIPTION OF THE INVENTION

Figure 1:
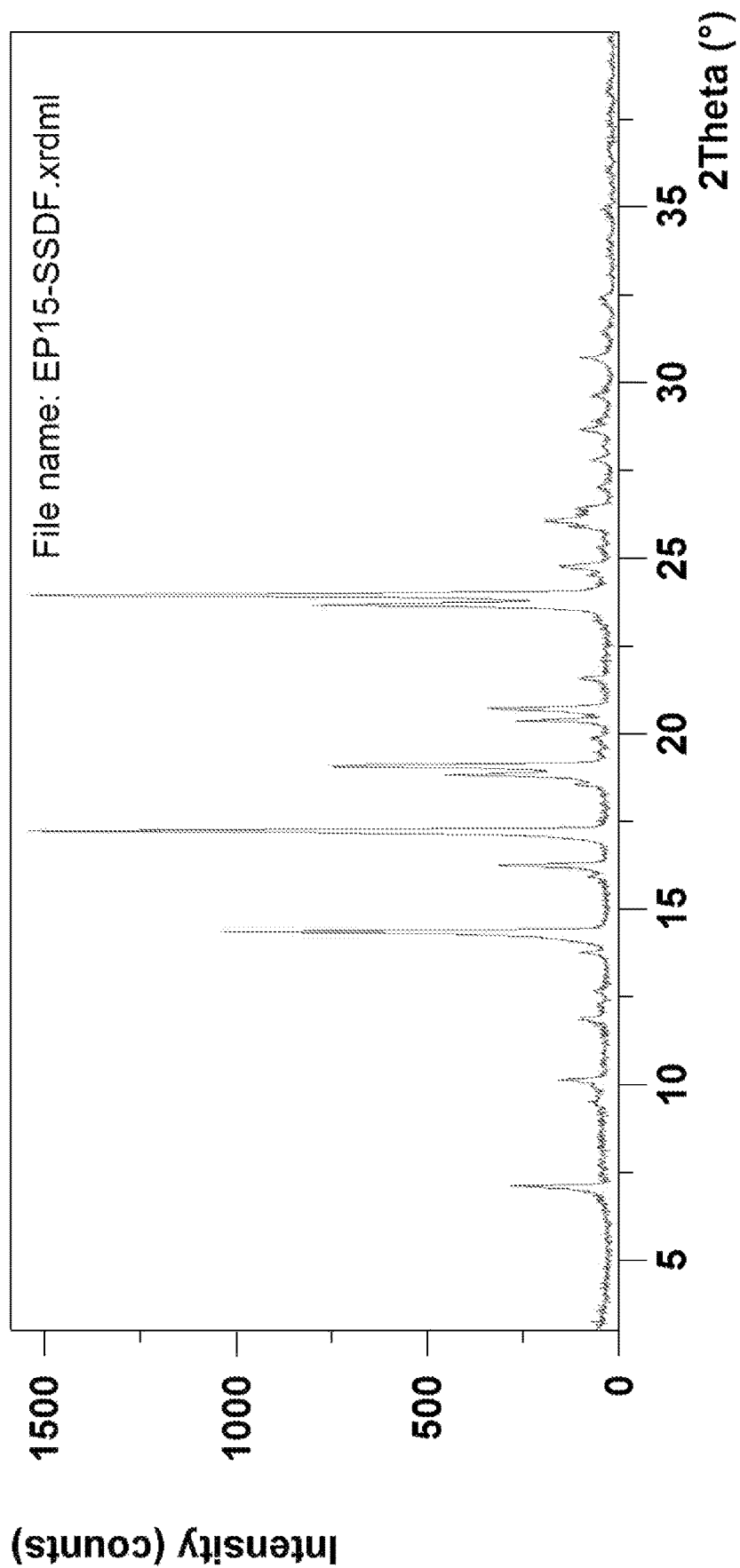
FIG. 1: X-Ray powder diffraction of example 0.

Compound 1-(4-(2-((1-(3,4-difluorophenyl)-1H-pyrazol-3-yl)methoxy)ethyl)piperazin-1-yl)ethanone is difficult to crystallize. On trying in different conditions, an oil was obtained in all the cases, either using precipitation or evaporation from several solvents. This oil crystallizes with seeding very slowly, and only after several days it gives a crystalline form. The difficulty to crystallize comes from its low melting point (46° C.). Thus there is a need for alternative forms of 1-(4-(2-((1-(3,4-difluorophenyl)-1H-pyrazol-3-yl)methoxy)ethyl)piperazin-1-yl)ethanone with a melting point higher than 46° C. which have advantages, among other, of simplifying the procedures of isolation, purification and handling.

Indeed, after an extensive screening of salts, it has been observed that a large number of acids (e.g. sulphuric acid, benzenesulphonic acid, acetic acid or L-tartaric acid) did not afford a solid when mixing with 1-(4-(2-((1-(3,4-difluorophenyl)-1H-pyrazol-3-yl)methoxy)ethyl)piperazin-1-yl)ethanone, but instead an oil was always obtained.

Further, among the acids suitable for obtaining a salt in solid form, it has been surprisingly found that the strong inorganic monoacids and the organic diacids were the ones that provided better results in terms of easiness of preparation, physical stability, scaling-up, solubility, etc. This is particularly true for hydrochloric acid and maleic acid. These results are shown through the increment achieved regarding the melting point and the values for some specific properties as thermodynamic solubility or pharmacokinetic parameters as Cmax or AUC in order to find new alternative forms having desirable properties for pharmaceutical use.

Thus, in one preferred aspect, the present invention is directed to a 1-(4-(2-((1-(3,4-difluorophenyl)-1H-pyrazol-3-yl)methoxy)ethyl)piperazin-1-yl)ethanone crystalline salt.

In another preferred aspect, the present invention is directed to 1-(4-(2-((1-(3,4-difluorophenyl)-1H-pyrazol-3-yl)methoxy)ethyl)piperazin-1-yl)ethanone crystalline salt selected from the group consisting of inorganic acids, sulphonic acids and organic acids.

In another preferred aspect, the present invention is directed to 1-(4-(2-((1-(3,4-difluorophenyl)-1H-pyrazol-3-yl)methoxy)ethyl)piperazin-1-yl)ethanone crystalline salt selected from the group consisting of hydrochloric acid and hydrobromic acid.

In another preferred aspect, the present invention is directed to 1-(4-(2-((1-(3,4-difluorophenyl)-1H-pyrazol-3-yl)methoxy)ethyl)piperazin-1-yl)ethanone crystalline salt selected from the group consisting of maleic acid, fumaric acid, oxalic acid, malonic acid and succinic acid.

In another preferred aspect, the present invention is directed to 1-(4-(2-((1-(3,4-difluorophenyl)-1H-pyrazol-3-yl)methoxy)ethyl)piperazin-1-yl)ethanone crystalline salt selected from the group consisting of hydrochloride, maleate, fumarate, malonate, succinate, oxalate and/or hydrobromide.

In a still more preferred aspect, the present invention is directed to 1-(4-(2-((1-(3,4-difluorophenyl)-1H-pyrazol-3-yl)methoxy)ethyl)piperazin-1-yl)ethanone hydrochloride and 1-(4-(2-((1-(3,4-difluorophenyl)-1H-pyrazol-3-yl) methoxy)ethyl)piperazin-1-yl) ethanone maleate.

As noted previously, it has been reported that 1-(4-(2-((1-(3,4-difluorophenyl)-1H-pyrazol-3-yl)methoxy)ethyl)piperazin-1-yl)ethanone is a highly selective sigma-1 ($\sigma_1$) receptor antagonist, displaying strong analgesic activity in the treatment and prevention of chronic and acute pain, and particularly, neuropathic pain (see WO 2011/147910).

It has now been found that 1-(4-(2-((1-(3,4-difluorophenyl)-1H-pyrazol-3-yl)methoxy)ethyl)piperazin-1-yl)ethanone crystalline salts are particularly suitable for use as medicament.

It has also been found that 1-(4-(2-((1-(3,4-difluorophenyl)-1H-pyrazol-3-yl)methoxy)ethyl)piperazin-1-yl)ethanone crystalline salt selected from the group consisting of inorganic acids, sulphonic acids and organic acids is particularly suitable for use as medicament.

It has also been found that 1-(4-(2-((1-(3,4-difluorophenyl)-1H-pyrazol-3-yl)methoxy)ethyl)piperazin-1-yl)ethanone crystalline salt selected from the group consisting of hydrochloric acid and hydrobromic acid is particularly suitable for use as medicament.

It has also been found that 1-(4-(2-((1-(3,4-difluorophenyl)-1H-pyrazol-3-yl)methoxy)ethyl)piperazin-1-yl)ethanone crystalline salt selected from the group consisting of maleic acid, fumaric acid, oxalic acid, malonic acid and succinic acid is particularly suitable for use as medicament.

It has also been found that 1-(4-(2-((1-(3,4-difluorophenyl)-1H-pyrazol-3-yl)methoxy)ethyl)piperazin-1-yl)ethanone crystalline salt selected from the group consisting of hydrochloride, maleate, fumarate, malonate, succinate, oxalate and/or hydrobromide is particularly suitable for use as medicament.

It has now been found that the hydrochloride salt of 1-(4-(2-((1-(3,4-difluorophenyl)-1H-pyrazol-3-yl)methoxy)ethyl)piperazin-1-yl)ethanone or the maleate salt of 1-(4-(2-((1-(3,4-difluorophenyl)-1H-pyrazol-3-yl)methoxy)ethyl) piperazin-1-yl)ethanone are particularly suitable for use as medicament.

The present invention therefore further provides medicaments or pharmaceutical compositions comprising a 1-(4-(2-((1-(3,4-difluorophenyl)-1H-pyrazol-3-yl)methoxy) ethyl)piperazin-1-yl)ethanone crystalline salt together with at least a pharmaceutically acceptable carrier, adjuvant, or vehicle, for administration to a patient.

The present invention therefore further provides medicaments or pharmaceutical compositions comprising a 1-(4-(2-((1-(3,4-difluorophenyl)-1H-pyrazol-3-yl)methoxy) ethyl)piperazin-1-yl)ethanone crystalline salt selected from the group consisting of inorganic acids, sulphonic acids and organic acids together with at least a pharmaceutically acceptable carrier, adjuvant, or vehicle, for administration to a patient.

The present invention therefore further provides medicaments or pharmaceutical compositions comprising a 1-(4-(2-((1-(3,4-difluorophenyl)-1H-pyrazol-3-yl)methoxy) ethyl)piperazin-1-yl)ethanone crystalline salt selected from the group consisting of hydrochloric acid and hydrobromic acid together with at least a pharmaceutically acceptable carrier, adjuvant, or vehicle, for administration to a patient.

The present invention therefore further provides medicaments or pharmaceutical compositions comprising a 1-(4-(2-((1-(3,4-difluorophenyl)-1H-pyrazol-3-yl)methoxy) ethyl)piperazin-1-yl)ethanone crystalline salt selected from the group consisting of maleic acid, fumaric acid, oxalic acid, malonic acid and succinic acid together with at least a pharmaceutically acceptable carrier, adjuvant, or vehicle, for administration to a patient.

The present invention therefore further provides medicaments or pharmaceutical compositions comprising a 1-(4-(2-((1-(3,4-difluorophenyl)-1H-pyrazol-3-yl)methoxy) ethyl)piperazin-1-yl)ethanone crystalline salt selected from the group consisting of hydrochloride, maleate, fumarate, malonate, succinate, oxalate and/or hydrobromide together with at least a pharmaceutically acceptable carrier, adjuvant, or vehicle, for administration to a patient.

The present invention therefore further provides medicaments or pharmaceutical compositions comprising 1-(4-(2-((1-(3,4-difluorophenyl)-1H-pyrazol-3-yl)methoxy) ethyl) piperazin-1-yl)ethanone hydrochloride or 1-(4-(2-((1-(3,4-difluorophenyl)-1H-pyrazol-3-yl)methoxy)ethyl)piperazin-1-yl)ethanone maleate together with at least a pharmaceutically acceptable carrier, adjuvant, or vehicle, for administration to a patient.

Examples of pharmaceutical compositions include any solid (tablets, pills, capsules, granules etc.) or liquid (solutions, suspensions or emulsions) composition for oral, topical or parenteral administration.

In a preferred embodiment the pharmaceutical compositions are in oral form, either solid or liquid. Suitable dose forms for oral administration may be tablets, capsules, syrops or solutions and may contain conventional excipients known in the art such as binding agents, for example syrup, acacia, gelatin, sorbitol, tragacanth, or polyvinylpyrrolidone; fillers, for example lactose, sugar, maize starch, calcium phosphate, sorbitol or glycine; tabletting lubricants, for example magnesium stearate; disintegrants, for example starch, polyvinylpyrrolidone, sodium starch glycollate or microcrystalline cellulose; or pharmaceutically acceptable wetting agents such as sodium lauryl sulfate.

The solid oral compositions may be prepared by conventional methods of blending, filling or tabletting. Repeated blending operations may be used to distribute the active agent throughout those compositions employing large quantities of fillers. Such operations are conventional in the art. The tablets may for example be prepared by wet or dry granulation and optionally coated according to methods well known in normal pharmaceutical practice, in particular with an enteric coating.

The pharmaceutical compositions may also be adapted for parenteral administration, such as sterile solutions, suspensions or lyophilized products in the appropriate unit dosage form. Adequate excipients can be used, such as bulking agents, buffering agents or surfactants.

Administration of the compounds or compositions of the present invention may be by any suitable method, such as intravenous infusion, oral preparations, and intraperitoneal and intravenous administration. Oral administration is preferred because of the convenience for the patient and the chronic character of the diseases to be treated.

The compounds and compositions of this invention may be used with other drugs to provide a combination therapy. The other drugs may form part of the same composition, or be provided as a separate composition for administration at the same time or at different time.

The auxiliary materials or additives of a pharmaceutical composition according to the present invention can be selected among carriers, excipients, support materials, lubricants, fillers, solvents, diluents, colorants, flavour conditioners such as sugars, antioxidants, binders, adhesives, disintegrants, anti-adherents, glidants and/or agglutinants. In the case of suppositories, this may imply waxes or fatty acid esters or preservatives, emulsifiers and/or carriers for parenteral application. The selection of these auxiliary materials and/or additives and the amounts to be used will depend on the form of application of the pharmaceutical composition.

The medicament or pharmaceutical composition according to the present invention may be in any form suitable for the application to humans and/or animals, preferably humans including infants, children and adults and can be produced by standard procedures known to those skilled in the art. Therefore, the formulation in accordance with the invention may be adapted for topical or systemic application, particularly for dermal, transdermal, subcutaneous, intramuscular, intra-articular, intraperito neal, intravenous, intra-arterial, intravesical, intraosseous, intracavernosal, pulmonary, buccal, sublingual, ocular, intravitreal, intranasal, percutaneous, rectal, vaginal, oral, epidural, intrathecal, intraventricular, intracerebral, intracerebroventricular, intra cisternal, intraspinal, perispinal, intracranial, delivery via needles or catheters with or without pump devices, or other application routes.

The mentioned formulations will be prepared using standard methods such as those described or referred to in the Spanish and US Pharmacopoeias and similar reference texts.

In one embodiment of the invention the 1-(4-(2-((1-(3,4-difluorophenyl)-1H-pyrazol-3-yl)methoxy)ethyl)piperazin-1-yl)ethanone crystalline salt is used in therapeutically effective amounts.

In another embodiment of the invention the 1-(4-(2-((1-(3,4-difluorophenyl)-1H-pyrazol-3-yl)methoxy)ethyl)piperazin-1-yl)ethanone crystalline salt selected from the group consisting of inorganic acids, sulphonic acids and organic acids is used in therapeutically effective amounts.

In another embodiment of the invention the 1-(4-(2-((1-(3,4-difluorophenyl)-1H-pyrazol-3-yl)methoxy)ethyl)piperazin-1-yl)ethanone crystalline salt selected from the group consisting of hydrochloric acid and hydrobromic acid is used in therapeutically effective amounts.

In another embodiment of the invention the 1-(4-(2-((1-(3,4-difluorophenyl)-1H-pyrazol-3-yl)methoxy)ethyl)piperazin-1-yl)ethanone crystalline salt selected from the group consisting of maleic acid, fumaric acid, oxalic acid, malonic acid and succinic acid is used in therapeutically effective amounts.

In a preferred embodiment of the invention the 1-(4-(2-((1-(3,4-difluorophenyl)-1H-pyrazol-3-yl)methoxy)ethyl)piperazin-1-yl)ethanone crystalline salt selected from the group consisting of hydrochloride, maleate, fumarate, malonate, succinate, oxalate and/or hydrobromide is used in therapeutically effective amounts.

In still more preferred embodiment of the invention the 1-(4-(2-((1-(3,4-difluorophenyl)-1H-pyrazol-3-yl)methoxy)ethyl)piperazin-1-yl)ethanone hydrochloride or the 1-(4-(2-((1-(3,4-difluorophenyl)-1H-pyrazol-3-yl)methoxy)ethyl)piperazin-1-yl)ethanone maleate are used in therapeutically effective amounts.

Generally an effective administered amount of a compound of the invention will depend on the relative efficacy of the compound chosen, the severity of the disorder being treated and the weight of the sufferer. The physician will determine the dosage of the present therapeutic agents which will be most suitable and it will vary with the form of administration and the particular compound chosen, and furthermore, it will vary with the patient under treatment, the age of the patient, the type of disease or condition being treated. When the composition is administered orally, larger quantities of the active agent will be required to produce the same effect as a smaller quantity given parenterally. The active compound will typically be administered once or more times a day for example 1, 2, 3 or 4 times daily, with typical total daily doses in the range of from 0.1 to 1000 mg/kg/day.

Particularly, 1-(4-(2-((1-(3,4-difluorophenyl)-1H-pyrazol-3-yl)methoxy)ethyl)piperazin-1-yl)ethanone crystalline salts are useful for the treatment and/or prophylaxis of a sigma receptor mediated disease or condition.

In a preferred embodiment the 1-(4-(2-((1-(3,4-difluorophenyl)-1H-pyrazol-3-yl)methoxy)ethyl)piperazin-1-yl) ethanone crystalline salts are used in the manufacture of a medicament for the treatment and/or prophylaxis of a disease selected from the group consisting of diarrhoea; lipoprotein disorders; migraine; obesity; arthritis; hypertension; arrhythmia; ulcer; learning, memory and attention deficits; cognition disorders; neurodegenerative diseases; demyelinating diseases; addiction to drugs and chemical substances including cocaine, amphetamine, ethanol and nicotine; tardive diskinesia; ischemic stroke; epilepsy; stroke; stress; cancer; psychotic conditions, in particular depression, anxiety or schizophrenia; inflammation; or autoimmune diseases.

In a still more preferred embodiment the 1-(4-(2-((1-(3,4-difluorophenyl)-1H-pyrazol-3-yl)methoxy)ethylpiperazin-1-yl)ethanone crystalline salts are used in the manufacture of a medicament for the treatment and/or prophylaxis of pain, preferably neuropathic pain, inflammatory pain or other pain conditions involving allodynia and/or hyperalgesia.

Particularly, 1-(4-(2-((1-(3,4-difluorophenyl)-1H-pyrazol-3-yl)methoxy)ethyl)piperazin-1-yl)ethanone crystalline salt selected from the group consisting of inorganic acids, sulphonic acids and organic acids is useful for the treatment and/or prophylaxis of a sigma receptor mediated disease or condition.

In a more preferred embodiment the 1-(4-(2-((1-(3,4-difluorophenyl)-1H-pyrazol-3-yl)methoxy)ethyl)piperazin-1-yl)ethanone crystalline salt selected from the group consisting of inorganic acids, sulphonic acids and organic acids is used in the manufacture of a medicament for the treatment and/or prophylaxis of a disease selected from the group consisting of diarrhoea; lipoprotein disorders; migraine; obesity; arthritis; hypertension; arrhythmia; ulcer; learning, memory and attention deficits; cognition disorders; neurodegenerative diseases; demyelinating diseases; addiction to drugs and chemical substances including cocaine, amphetamine, ethanol and nicotine; tardive diskinesia; ischemic stroke; epilepsy; stroke; stress; cancer; psychotic conditions, in particular depression, anxiety or schizophrenia; inflammation; or autoimmune diseases.

In a still more preferred embodiment the 1-(4-(2-((1-(3,4-difluorophenyl)-1H-pyrazol-3-yl)methoxy)ethylpiperazin-1-yl)ethanone crystalline salt selected from the group consisting of inorganic acids, sulphonic acids and organic acids is used in the manufacture of a medicament for the treatment and/or prophylaxis of pain, preferably neuropathic pain, inflammatory pain or other pain conditions involving allodynia and/or hyperalgesia.

Particularly, 1-(4-(2-((1-(3,4-difluorophenyl)-1H-pyrazol-3-yl)methoxy)ethyl)piperazin-1-yl)ethanone crystalline salt selected from the group consisting of is selected from the group consisting of hydrochloric acid and hydrobromic acid is useful for the treatment and/or prophylaxis of a sigma receptor mediated disease or condition.

In a more preferred embodiment the 1-(4-(2-((1-(3,4-difluorophenyl)-1H-pyrazol-3-yl)methoxy)ethyl)piperazin- 1-yl)ethanone crystalline salt is selected from the group consisting of hydrochloric acid and hydrobromic acid is used in the manufacture of a medicament for the treatment and/or prophylaxis of a disease selected from the group consisting of diarrhoea; lipoprotein disorders; migraine; obesity; arthritis; hypertension; arrhythmia; ulcer; learning, memory and attention deficits; cognition disorders; neurodegenerative diseases; demyelinating diseases; addiction to drugs and chemical substances including cocaine, amphetamine, ethanol and nicotine; tardive diskinesia; ischemic stroke; epilepsy; stroke; stress; cancer; psychotic conditions, in particular depression, anxiety or schizophrenia; inflammation; or autoimmune diseases.

In a still more preferred embodiment the 1-(4-(2-((1-(3,4-difluorophenyl)-1H-pyrazol-3-yl)methoxy)ethyl)piperazin-1-yl)ethanone crystalline salt is selected from the group consisting of hydrochloric acid and hydrobromic acid is used in the manufacture of a medicament for the treatment and/or prophylaxis of pain, preferably neuropathic pain, inflammatory pain or other pain conditions involving allodynia and/or hyperalgesia.

Particularly, 1-(4-(2-((1-(3,4-difluorophenyl)-1H-pyrazol-3-yl)methoxy)ethyl)piperazin-1-yl)ethanone crystalline salt selected from the group consisting of selected from the group consisting of maleic acid, fumaric acid, oxalic acid, malonic acid and succinic acid is useful for the treatment and/or prophylaxis of a sigma receptor mediated disease or condition.

In a more preferred embodiment the 1-(4-(2-((1-(3,4-difluorophenyl)-1H-pyrazol-3-yl)methoxy)ethyl)piperazin-1-yl)ethanone crystalline salt selected from the group consisting of maleic acid, fumaric acid, oxalic acid, malonic acid and succinic acid is used in the manufacture of a medicament for the treatment and/or prophylaxis of a disease selected from the group consisting of diarrhoea; lipoprotein disorders; migraine; obesity; arthritis; hypertension; arrhythmia; ulcer; learning, memory and attention deficits; cognition disorders; neurodegenerative diseases; demyelinating diseases; addiction to drugs and chemical substances including cocaine, amphetamine, ethanol and nicotine; tardive diskinesia; ischemic stroke; epilepsy; stroke; stress; cancer; psychotic conditions, in particular depression, anxiety or schizophrenia; inflammation; or autoimmune diseases.

In a still more preferred embodiment the 1-(4-(2-((1-(3,4-difluorophenyl)-1H-pyrazol-3-yl)methoxy)ethyl)piperazin-1-yl)ethanone crystalline salt selected from the group consisting of maleic acid, fumaric acid, oxalic acid, malonic acid and succinic acid is used in the manufacture of a medicament for the treatment and/or prophylaxis of pain, preferably neuropathic pain, inflammatory pain or other pain conditions involving allodynia and/or hyperalgesia.

Particularly, 1-(4-(2-((1-(3,4-difluorophenyl)-1H-pyrazol-3-yl)methoxy)ethyl)piperazin-1-yl)ethanone crystalline salt selected from the group consisting of hydrochloride, maleate, fumarate, malonate, succinate, oxalate and/or hydrobromide is useful for the treatment and/or prophylaxis of a sigma receptor mediated disease or condition.

In a more preferred embodiment the 1-(4-(2-((1-(3,4-difluorophenyl)-1H-pyrazol-3-yl)methoxy)ethyl)piperazin-1-yl)ethanone crystalline salt selected from the group consisting of hydrochloride, maleate, fumarate, malonate, succinate, oxalate and/or hydrobromide is used in the manufacture of a medicament for the treatment and/or prophylaxis of a disease selected from the group consisting of diarrhoea; lipoprotein disorders; migraine; obesity; arthritis; hypertension; arrhythmia; ulcer; learning, memory and attention deficits; cognition disorders; neurodegenerative diseases; demyelinating diseases; addiction to drugs and chemical substances including cocaine, amphetamine, ethanol and nicotine; tardive diskinesia; ischemic stroke; epilepsy; stroke; stress; cancer; psychotic conditions, in particular depression, anxiety or schizophrenia; inflammation; or autoimmune diseases.

In a still more preferred embodiment the 1-(4-(2-((1-(3,4-difluorophenyl)-1H-pyrazol-3-yl)methoxy)ethyl)piperazin-1-yl)ethanone crystalline salt selected from the group consisting of hydrochloride, maleate, fumarate, malonate, succinate, oxalate and/or hydrobromide is used in the manufacture of a medicament for the treatment and/or prophylaxis of pain, preferably neuropathic pain, inflammatory pain or other pain conditions involving allodynia and/or hyperalgesia.

More particularly, 1-(4-(2-((1-(3,4-difluorophenyl)-1H-pyrazol-3-yl)methoxy)ethyl)piperazin-1-yl)ethanone hydrochloride or 1-(4-(2-((1-(3,4-difluorophenyl)-1H-pyrazol-3-yl)methoxy)ethyl)piperazin-1-yl)ethanone maleate are useful for the treatment and/or prophylaxis of a sigma receptor mediated disease or condition.

In a more preferred embodiment the 1-(4-(2-((1-(3,4-difluorophenyl)-1H-pyrazol-3-yl)methoxy)ethyl)piperazin-1-yl)ethanone hydrochloride or the 1-(4-(2-((1-(3,4-difluorophenyl)-1H-pyrazol-3-yl)methoxy)ethyl)piperazin-1-yl)ethanone maleate are used in the manufacture of a medicament for the treatment and/or prophylaxis of a disease selected from the group consisting of diarrhoea; lipoprotein disorders; migraine; obesity; arthritis; hypertension; arrhythmia; ulcer; learning, memory and attention deficits; cognition disorders; neurodegenerative diseases; demyelinating diseases; addiction to drugs and chemical substances including cocaine, amphetamine, ethanol and nicotine; tardive diskinesia; ischemic stroke; epilepsy; stroke; stress; cancer; psychotic conditions, in particular depression, anxiety or schizophrenia; inflammation; or autoimmune diseases.

In a still more preferred embodiment the 1-(4-(2-((1-(3,4-difluorophenyl)-1H-pyrazol-3-yl)methoxy)ethyl)piperazin-1-yl)ethanone hydrochloride or the 1-(4-(2-((1-(3,4-difluorophenyl)-1H-pyrazol-3-yl)methoxy)ethyl)piperazin-1-yl)ethanone maleate are used in the manufacture of a medicament for the treatment and/or prophylaxis of pain, preferably neuropathic pain, inflammatory pain or other pain conditions involving allodynia and/or hyperalgesia.

The following examples are merely illustrative of certain embodiments of the invention and cannot be considered as restricting it in any way.

EXAMPLES

Analytical Techniques

The following techniques have been used in this invention for identifying either 1-(4-(2-((1-(3,4-difluorophenyl)-1H-pyrazol-3-yl)methoxy)ethyl)piperazin-1-yl) ethanone or its different salts obtained:

Proton Nuclear Magnetic Resonance ($^1$H-NMR) Proton nuclear magnetic resonance analyses were recorded in deuterated methanol ($CD_3OD$) in a Varian Mercury 400 spectrometer, equipped with a broadband probe ATB 1H/19F/X of 5 mm. Spectra were acquired dissolving 5-10 mg of sample in 0.7 mL of deuterated solvent.

X-Ray Powder Diffraction (XRPD) characterization XRPD analysis was performed using a Philips X'Pert diffractometer with Cu Kα radiation in Bragg-Brentano geometry. The system is equipped with a monodimensional, real time multiple strip detector. Diffractograms were recorded from 3° to 40° (2θ) at a scan rate of 17.6° per minute.

Differential Scanning calorimetry analysis (DSC)

DSC analyses were recorded in a Mettler Toledo DSC822e. Samples of 1-2 mg were weighted into 40 μl aluminum crucibles with a pinhole lid, and were heated, under nitrogen (50 mL/min), from 30 to 300° C. at a heating rate of 10° C./min. Data collection and evaluation were done with software STARe.

Example 0

Figure 2:
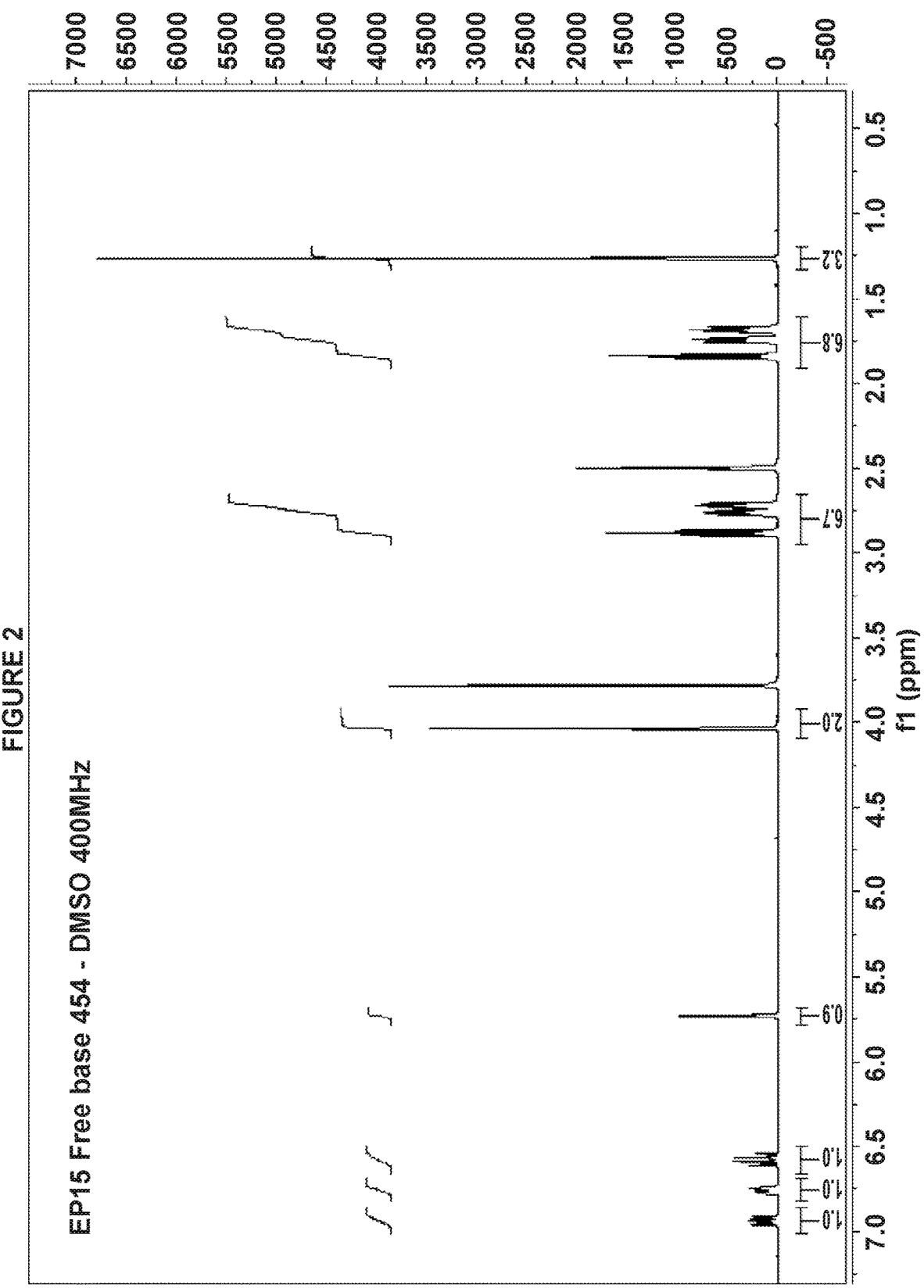
FIG. 2: $^1$H nuclear magnetic resonance of example 0.

Characterization of 1-(4-(2-((1-(3,4-difluorophenyl)-1H-pyrazol-3-yl) methoxy)ethyl)piperazin-1-yl)ethanone Example 0 can be prepared as disclosed in the previous patent application WO 2011/147910 and was characterized by X-Ray powder diffraction (FIG. 1) and by $^1$H nuclear magnetic resonance (FIG. 2).

Alternatively, example 0 can be obtained as follows:

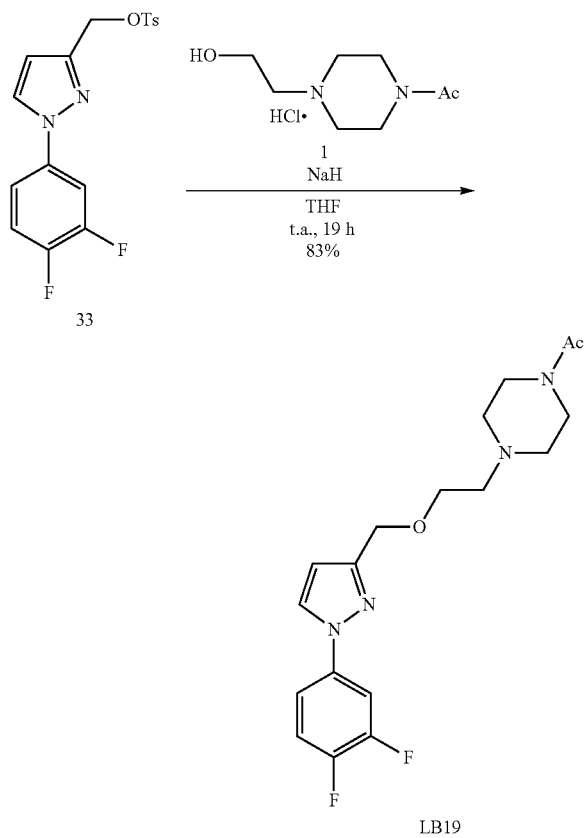

To a suspension of 1-(4-(2-hydroxyethyl)piperazin-1-yl)ethanone (1) (16.98 g, 81.3 mmol) in tetrahydrofuran (150 mL) at 0° C., NaH (60% mineral oil, 8.13 g, 203.4 mmol) was added turing 15 min. The mixture was stirred for 10 min and (1-(3,4-difluorophenyl)-1H-pyrazol-3-yl)methyl 4-methylbenzenesulfonate (33) (24.70 g, 67.8 mmol) in tetrahydrofuran (200 mL) was added during 25 min. The suspension was allowed to reach room temperature and stirred for 19 h. The mixture was cooled to 0° C. and H$_2$O (15 mL) was slowly added. The suspension was allowed to reach room temperature and stirred for 10 min. Ethyl acetate (350 mL) and saturated aqueous NH$_4$Cl solution (300 mL), were added to the mixture and the phases separated. The aqueous phase was extracted with ethyl acetate (1×250 mL), and the combined organic phases were washed with saturated aqueous NaHCO$_3$ solution (2×400 mL), dried over anhydrous Na$_2$SO$_4$ and filtered. The solvent was removed and the crude orange oil thus obtained was purified by chromatography over silica-gel (CH$_2$Cl$_2$/MeOH/NH$_4$OH 98:2:1-95:5:1), to give the title compound (LB19) as an orange solid (20.50 g, 83% yield).

General Method for Obtaining Salts of Example 0

Previously a solubility study was performed with compound Example 0. The results are shown in Table 1 wherein number of volumes needed to dissolve the solid in the corresponding solvent at room temperature is shown. If at 50 volumes, dissolution was not observed at room temperature, mixture was heated to reflux temperature.

TABLE 1

| Example 0 compound solubility | |
|---|---|
| Product | Example 0 |
| H$_2$O | 50[1] |
| CH$_3$CN | 15 |
| EtOH | 4 |
| MIBK | 17 |
| THF | 4 |
| CH$_2$Cl$_2$ | 3 |

[1]No dissolution was observed at room temperature and included when mixture was heated to reflux temperature.

The acids used to investigate the crystalline salts of example 0 were selected according to the following criteria:

Acids with enough acidity to protonate the example 0

Acids that are pharmaceutically acceptable compounds

The selection of the acids was then carried out starting from the list in P. H. Stahl, C. G. Wemuth, *Handbook of Pharmaceutical Salts: Properties, Selection and Use* 2002. Acids having a pKa low enough to form a salt with example 0 (pKa(base)−pKa(acid)>3) were chosen and are shown in table 2

TABLE 2

| Acid | Purity (%) | pKa$_1$ | pKa$_2$ | pKa$_3$ |
|---|---|---|---|---|
| Phosphoric acid | — | 2.15 | 7.20 | 12.35 |
| Maleic acid | 99.3 | 1.92 | 6.23 | — |
| Benzensulphonic acid | — | 0.7 | — | — |
| Sulfuric acid | — | Strong | 1.99 | — |
| Acetic acid | — | 4.75 | — | — |
| Propanoic acid | — | 4.87 | — | — |
| Methanesulfonic acid | — | −1.2 | — | — |
| Ethanesulfonic acid | — | 2.05 | — | — |
| Benzoic acid | — | 4.2 | — | — |
| Cinnamic acid | — | 4.44 | — | — |
| Nicotinic acid | — | 4.85 | — | — |
| Salicylic acid | — | 2.97 | — | — |
| Capric acid | — | 4.9 | — | — |
| Caproic acid | — | 4.88 | — | — |
| Caprylic acid | — | 4.89 | — | — |
| Citric acid | — | 3.13 | 4.76 | 6.40 |
| Fumaric acid | 100 | 3.03 | 4.38 | — |
| Malonic acid | 100 | 2.83 | 5.70 | — |
| Oxalic acid | 100 | 1.25 | 4.27 | — |
| Succinic acid | 100 | 4.21 | 5.64 | — |
| L-(+)-Tartaric acid | — | 3.02 | 4.36 | — |
| Hydrobromic acid | 100 | Strong | — | — |

TABLE 2-continued

| Acid | Purity (%) | pKa$_1$ | pKa$_2$ | pKa$_3$ |
|---|---|---|---|---|
| Nitric acid | — | Strong | — | — |
| Hydrochloric acid | 99.4 | Strong | — | — |

Although several of the acids selected have two or even three (citric acid) acidic positions, in principle, only sulfuric acid has a second proton acidic enough to form the disalt with example 0. In total there are twenty four different salts that could be formed.

Experimental Part:

General Experimental Conditions:

Wet Grinding Experiments:

General procedure: In a microtube of 2 mL, Example 0 and 1 eq. of the corresponding acid were added. One drop of solvent and two steel balls were added to each tube and the resulting mixture was grinded in a ball mill (15 min, 30 Hz, three times) and dried. In case of liquid acids, an ethyl acetate solution was previously prepared and the necessary volume for 1 eq of acid was added to the microtube.

Results obtained are shown in Table 3

TABLE 3

| Acid | Solvent | Observation | XRPD Result |
|---|---|---|---|
| Benzenesulfonic acid | H$_2$O | Yellow oil | Amorphous |
| Benzenesulfonic acid | CH$_3$CN | Yellow oil | Amorphous |
| Benzenesulfonic acid | THF | Yellow oil | Amorphous |
| Benzenesulfonic acid | EtOH | Yellow oil | Amorphous |
| Benzenesulfonic acid | Heptane | Pastous solid | Amorphous |
| Benzenesulfonic acid | Et$_2$O | Pastous solid | Amorphous |
| Benzenesulfonic acid | Cyclohexane | Pastous solid | Amorphous |
| Benzensulphonic acid | EtOH—Et$_2$O | Pastous solid | Amorphous |
| Benzensulphonic acid | CH$_2$Cl$_2$ | Pastous solid | Amorphous |
| Benzensulphonic acid | MIBK | Pastous solid | Amorphous |
| Benzensulphonic acid | Heptane | Pastous solid | Amorphous |
| Benzensulphonic acid | Toluene | Pastous solid | Amorphous |
| Maleic acid | MIBK | Yellow oil | Amorphous |
| Maleic acid | CH$_2$Cl$_2$ | Yellow oil | Amorphous |
| Maleic acid | EtOH | Off White pastous solid | Example 2 |
| Maleic acid | Cyclohexane | White solid | Example 2 |
| Maleic acid | Heptane | White solid | Example 2 |
| Maleic acid | Et$_2$O | White solid | Example 2 |
| Maleic acid | MTBE | White solid | Example 2 |
| Maleic acid | MTBE | White solid | Example 2 |
| Maleic acid | MTBE | White solid | Example 2 |
| Maleic acid | H$_2$O | no crystallisation | — |
| Maleic acid | CH$_3$CN—Et$_2$O | Pastous solid | Amorphous |
| Maleic acid | THF | White solid | Example 2 |
| Fumaric acid | THF | White solid | Example 3 |
| Fumaric acid | IPA | White solid | Example 3 |
| Fumaric acid | EtOH | Yellow oil | — |
| Fumaric acid | IPA | White solid | Example 3 |
| Fumaric acid | IPA | Off white solid | Example 3 |
| Malonic acid | MIBK | White solid | Example 4 |
| Malonic acid | MTBE | White solid | Example 4 (low crystallinity) |
| Malonic acid | Et$_2$O | White solid | Example 4 (low crystallinity) |
| Malonic acid | Ether | White solid | Example 4 |
| Malonic acid | MIBK | White solid | Example 4 |
| Malonic acid | EtOH | Yellow oil | — |
| Malonic acid | CHCl$_3$ | Yellow paste | — |
| Capric acid | H$_2$O | Yellowish oil | — |
| Capric acid | CH$_3$CN | Yellowish oil | — |
| Capric acid | CHCl$_3$ | Yellowish oil | — |
| Capric acid | AcOEt | Yellowish oil | — |
| Capric acid | MTBE | brown paste | — |
| Capric acid | Toluene | brown oil | — |
| Capric acid | CH$_3$CN | Off white pastous solid | Amorphous |
| Capric acid | EtOH | Yellow oil | — |
| Capric acid | H$_2$O/AcO$^t$Bu | Yellow oil | — |
| Capric acid | CH$_3$CN/MIBK | Yellow oil | — |
| Capric acid | CH$_2$Cl$_2$ | Yellow oil | — |
| Sulphuric acid | H$_2$O | oil | — |
| Sulphuric acid | CH$_3$CN | oil | — |
| Sulphuric acid | IPA | oil | — |
| Sulphuric acid | H$_2$O | oil | — |
| Sulphuric acid | Heptane | oil | Amorphous |
| Sulphuric acid | Acetone | oil | Amorphous |
| Succinic acid | MIBK | White solid | Example 6 |
| Succinic acid | MIBK | White solid | Example 6 |
| Succinic acid | MTBE | Off white solid | Example 6 |
| Succinic acid | MIBK | White solid | Example 6 |
| Succinic acid | H$_2$O | Paste | Example 6 (low crystallinity) |
| Succinic acid | CH$_3$CN | White solid | Example 6 |
| Succinic acid | MTBE | White solid | Example 6 |

TABLE 3-continued

| Acid | Solvent | Observation | XRPD Result |
|---|---|---|---|
| Succinic acid | AcOEt | White solid | Example 6 |
| Succinic acid | EtOH | Off white pastous solid | Amorphous |
| Succinic acid | EtOH | Yellow oil | — |
| Succinic acid | MIBK | White solid | Example 6 |
| Caprylic acid | $CH_2Cl_2$ | brown oil | — |
| Caprylic acid | $Et_2O$ | brown oil | — |
| Caprylic acid | AcOEt | Yellow oil | — |
| Caprylic acid | Heptane | Colorless solution | — |
| Caprylic acid | AcOEt | Yellow oil | — |
| Caproic acid | AcOEt | Yellow oil | — |
| Caproic acid | Toluene | brown oil | — |
| Caproic acid | /Heptane | Colorless solution | — |
| Caproic acid | AcOEt | Yellow oil | — |
| Caproic acid | $Et_2O$ | brown oil | — |
| Caproic acid | $CH_2Cl_2$ | brown oil | — |
| Propionic acid | $CH_2Cl_2$ | brown oil | — |
| Propionic acid | $Et_2O$ | brown oil | — |
| Propionic acid | AcOEt | Yellow oil | — |
| Propionic acid | Toluene | brown oil | — |
| Propionic acid | AcOEt | Yellow oil | — |
| Propionic acid | Heptane | Brown oil | — |
| Phosphoric acid | Dioxane | oil | Amorphous |
| Phosphoric acid | EtOH | oil | Amorphous |
| Methanesulfonic acid | AcOEt | Yellow oil | — |
| Methanesulfonic acid | $CH_2Cl_2$ | brown oil | — |
| Methanesulfonic acid | Toluene | Greenish paste | Amorphous |
| Methanesulfonic acid | $Et_2O$ | brown oil | — |
| Methanesulfonic acid | AcOEt | Yellow oil | — |
| Methanesulfonic acid | Toluene | yellow oil | — |
| Methanesulfonic acid | Heptane | Brown oil | — |
| Methanesulfonic acid | Cyclohexane | Yellow oil | — |
| Ethanesulfonic acid | Cyclohexane | Yellow oil | — |
| Ethanesulfonic acid | Heptane | Brown oil | — |
| Ethanesulfonic acid | $Et_2O$ | brown oil | — |
| Ethanesulfonic acid | $CH_2Cl_2$ | brown oil | — |
| Ethanesulfonic acid | Toluene | Greenish paste | Amorphous |
| Ethanesulfonic acid | AcOEt | Yellow oil | — |
| Ethanesulfonic acid | Toluene | yellow oil | — |
| Ethanesulfonic acid | AcOEt | Yellow oil | — |
| Salicylic acid | $H_2O$ | Yellowish oil | — |
| Salicylic acid | AcOEt | Yellowish oil | — |
| Salicylic acid | $CH_2Cl_2$ | Yellowish oil | — |
| Salicylic acid | $CH_2Cl_2$ | Yellow oil | — |
| Salicylic acid | Toluene | Reddish oil | — |
| Salicylic acid | $CH_3CN$ | Yellow oil | — |
| Salicylic acid | MTBE | Off white solid | Amorphous |
| Salicylic acid | AcOEt | Yellow oil | — |
| Salicylic acid | $CH_2Cl_2$ | Reddish oil | — |
| Salicylic acid | Toluene | Brown oil | — |
| Salicylic acid | EtOH | Yellow oil | — |
| Salicylic acid | toluene/cyclohexane | Yellow paste | Amorphous |
| Salicylic acid | MTBE/cyclohexane | Yellow paste | Salicylic acid |
| Salicylic acid | Cyclohexane | Yellowish paste | Amorphous |
| Salicylic acid | Cyclohexane | Off white pastous solid | Amorphous |
| Salicylic acid | $CH_3CN$ | Yellowish oil | — |
| Salicylic acid | MTBE | Yellowish oil | — |
| Nicotinic acid | $H_2O$ | White paste | Nicotinic acid |
| Nicotinic acid | $CH_3CN$ | Yellowish oil | — |
| Nicotinic acid | MTBE | Yellowish oil | — |
| Nicotinic acid | AcOEt | Yellowish oil | — |
| Nicotinic acid | $CH_2Cl_2$ | Yellowish oil | — |
| Nicotinic acid | MTBE | Off white pastous solid | Nicotinic acid |
| Nicotinic acid | $CH_2Cl_2$ | White solid | Nicotinic acid |
| Nicotinic acid | IPA | Off white solid | Nicotinic acid |
| Nicotinic acid | $CH_3CN$ | Off white solid | Nicotinic acid |
| Nicotinic acid | MTBE | Off white solid | Nicotinic acid |
| Nicotinic acid | AcOEt | Off white solid | Nicotinic acid |
| Nicotinic acid | $CH_2Cl_2$ | Off white solid | Nicotinic acid |
| Nicotinic acid | MTBE | White solid | Nicotinic acid |
| Nicotinic acid | EtOH | Yellow solid | Amorphous + nicotinic acid |

TABLE 3-continued

| Acid | Solvent | Observation | XRPD Result |
|---|---|---|---|
| Nicotinic acid | CH₃CN | White solid | Nicotinic acid |
| Nicotinic acid | IPA | White solid | Nicotinic acid |
| Citric acid | Toluene | Yellow oil | — |
| Citric acid | CH₃CN | Yellow oil | — |
| Citric acid | MTBE | Off white solid | Amorphous |
| Citric acid | AcOEt | Yellow oil | — |
| Citric acid | CH₂Cl₂ | Yellow oil | — |
| Citric acid | CH₃CN | Brown oil | — |
| Citric acid | MIBK | Off white solid | Citric acid |
| Citric acid | EtOH | Yellow oil | — |
| Citric acid | Et₂O | Yellowish paste | Amorphous |
| Citric acid | AcOEt | Yellow solidl | Citric acid |
| Citric acid | CH₃CN/cyclohexane | Off white paste | Amorphous |
| Citric acid | H₂O | Yellowish oil | — |
| Citric acid | CH₃CN | Yellowish oil | — |
| Citric acid | MTBE | Yellowish oil | — |
| Citric acid | AcOEt | Yellowish oil | — |
| Citric acid | CH₂Cl₂ | Yellowish oil | — |
| Citric acid | CH₂Cl₂ | Yellow oil | — |
| Citric acid | Et₂O | Off white pastous solid | Amorphous |
| Benzoic acid | MTBE | Off white pastous solid | Amorphous |
| Benzoic acid | H₂O/AcO^iBu | Yellow oil | — |
| Benzoic acid | CH₃CN/MIBK | Yellow oil | — |
| Benzoic acid | CHCl₃/Toluene | Off white solid | Example 1 |
| Benzoic acid | AcOEt/Heptane | Yellow paste/oil | Amorphous |
| Benzoic acid | Et₂O | Yellow paste/oil | — |
| Benzoic acid | CH₂Cl₂ | Yellow oil | — |
| Benzoic acid | EtOH | Brown oil | — |
| Benzoic acid | MTBE | brown oil | — |
| Benzoic acid | H₂O | Yellowish oil | — |
| Benzoic acid | CH₃CN | Yellowish oil | — |
| Benzoic acid | CHCl₃ | Yellowish oil | — |
| Benzoic acid | AcOEt | Yellowish oil | — |
| Cinnamic acid | MTBE | Off white pastous solid | Amorphous |
| Cinnamic acid | MTBE | brown oil | — |
| Cinnamic acid | CH₂Cl₂ | Brown oil | — |
| Cinnamic acid | H2O | Yellowish oil | — |
| Cinnamic acid | CH₃CN | Yellowish oil | — |
| Cinnamic acid | CHCl₃ | Yellowish oil | — |
| Cinnamic acid | AcOEt | Yellowish oil | — |
| Cinnamic acid | H₂O/AcO^iBu | Yellow oil | — |
| Cinnamic acid | CH₃CN/MIBK | Brown oil | — |
| Cinnamic acid | AcOEt/Heptane | Yellow paste/oil | Amorphous |
| Cinnamic acid | Et₂O | Yellow paste/oil | — |
| Cinnamic acid | EtOH | Yellow oil | — |
| Oxalic acid | MTBE | White solid | Example 5 |
| Oxalic acid | AcOiBu | White solid | Example 5 |
| Oxalic acid | EtOH | White solid | Example 5 |
| Oxalic acid | IPA | White solid | Example 5 |
| Oxalic acid | MIBK | White solid | Example 5 |
| Oxalic acid | AcOEt | White solid | Example 5 |
| Oxalic acid | AcOEt | White solid | Example 5 |
| Oxalic acid | AcOEt | White solid | Example 5 |
| Oxalic acid | MIBK | Off white solid | Example 5 |
| Oxalic acid | MIBK | Off white solid | Example 5 |
| Oxalic acid | MIBK | Off white solid | Example 5 |
| Hydrobromic acid | Cyclohexane | Yellow oil | — |
| Hydrobromic acid | IPA | Brown paste | Amorphous |
| Hydrobromic acid | CH₃CN | Brown paste | Amorphous |
| Hydrobromic acid | Acetone | Brown paste | Amorphous |
| Hydrobromic acid | IPA | Brown paste | Amorphous |
| Hydrobromic acid | CH₃CN | Brown paste | Amorphous |
| Hydrobromic acid | Acetone | Brown paste | Amorphous |
| Hydrobromic acid | Toluene | No evolution | — |
| Hydrobromic acid | MIBK/IPA | White solid | Example 7 |
| Hydrobromic acid | THF/IPA | White solid | Example 7 |
| Hydrobromic acid | MTBE/IPA | White solid | Example 7 |
| Hydrobromic acid | Toluene/IPA | White solid | Example 7 |

TABLE 3-continued

| Acid | Solvent | Observation | XRPD Result |
|---|---|---|---|
| Hydrobromic acid | MIBK/IPA | White solid | Example 7 |
| Hydrobromic acid | IPA | Yellow liquid | — |
| Hydrobromic acid | $CH_3CN$ | Yellow oil | — |
| Hydrobromic acid | Acetone | Yellow oil | — |
| Hydrobromic acid | THF | brown oil | — |
| Tartaric acid | $AcO^iBu$ | Off white solid | Tartaric acid |
| Tartaric acid | MIBK | Off white solid | Tartaric acid |
| Tartaric acid | $Et_2O$ | Off white solid | Tartaric acid |
| Tartaric acid | Toluene | Off white solid | Tartaric acid |
| Tartaric acid | MIBK | Off white solid | Tartaric acid |
| Tartaric acid | $CHCl_3$ | Yellow oil | — |
| Tartaric acid | $CH_3CN$ | Yellow oil | — |
| Tartaric acid | THF | Yellow oil | — |
| Tartaric acid | Dioxane | Off white solid | Amorphous |
| Tartaric acid | $H_2O$ | yellow oil | — |
| Tartaric acid | Acetone | Yellow oil | — |
| Tartaric acid | $CH_3CN$ | Oil + solvent | — |
| Tartaric acid | EtOH | Yellow oil | — |
| Tartaric acid | $H_2O$ | Off white pastous solid | Amorphous |
| Tartaric acid | $CH_3CN$ | Off white pastous solid | Amorphous |
| Tartaric acid | THF | Off white pastous solid | Amorphous |
| Tartaric acid | MTBE | Off white pastous solid | Amorphous |
| Tartaric acid | EtOH | Off white pastous solid | Amorphous |
| Tartaric acid | MIBK | Yellowish paste | Amorphous |
| Nitric acid | Toluene | No evolution | — |
| Nitric acid | MTBE | No evolution | — |
| Nitric acid | AcOEt | No evolution | — |
| Nitric acid | Cyclohexane | Yellow oil | — |
| Nitric acid | IPA | Yellow liquid | — |
| Nitric acid | $CH_3CN$ | Yellow oil | — |
| Nitric acid | Acetone | Yellow oil | — |
| Nitric acid | THF | yellow oil | — |
| Acetic acid | AcOEt | Yellow oil | — |
| Acetic acid | $Et_2O$ | brown oil | — |
| Acetic acid | AcOEt | Yellow oil | — |
| Acetic acid | $CH_2Cl_2$ | brown oil | — |
| Acetic acid | Toluene | brown oil | — |
| Acetic acid | MTBE | No evolution | — |

Where MIBK stands for methyl isobutyl ketone, MTBE stands for methyl tert-butylether, IPA stands for isopropanol and THF stands for tetrahydrofuran.

From the above experiments and the corresponding DSC data, as shown in Table 4, it can be concluded that increasing melting point regarding 1-(4-(2-((1-(3,4-difluorophenyl)-1H-pyrazol-3-yl)methoxy)ethyl)piperazin-1-yl)ethanone (example 0) is achieved in order to find new alternative forms having desirable properties for pharmaceutical use.

TABLE 4

| Example no | Acid Structure | Acid Name | MP (° C.) DSC |
|---|---|---|---|
| 1 | HCl | Hydrochloric acid | 155-157 |
| 2 | Cis-HOOC—CH=CH—COOH | Maleic acid | 160-162 |
| 3 | Trans-HOOC—CH=CH—COOH | Fumaric acid | 132-133 |
| 4 | HOOC—$CH_2$—COOH | Malonic acid | 101-103 |
| 5 | HOOC—COOH | Oxalic acid | 160-162 |
| 6 | HOOC—$CH_2$—$CH_2$—COOH | Succinic acid | 102-104 |
| 7 | HBr | Hydrobromic acid | 170-171 |

Example 0 MP: 46° C.

The above mentioned examples 1 to 7 can be specifically obtained according to the following procedures:

Example 1

Synthesis of 1-acetyl-4-({[1-(3,4-difluorophenyl)-1H-pyrazol-3-yl]methoxy}methyl)piperazine hydrochloride

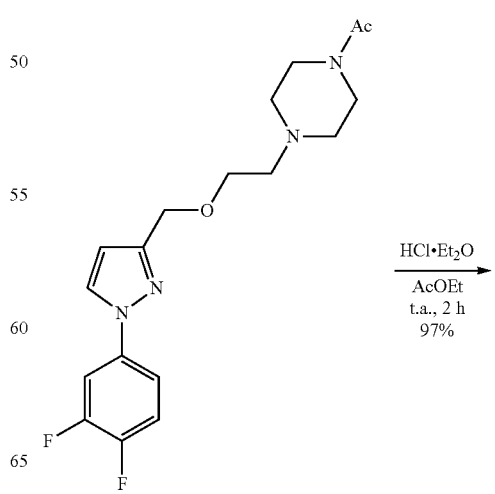

-continued

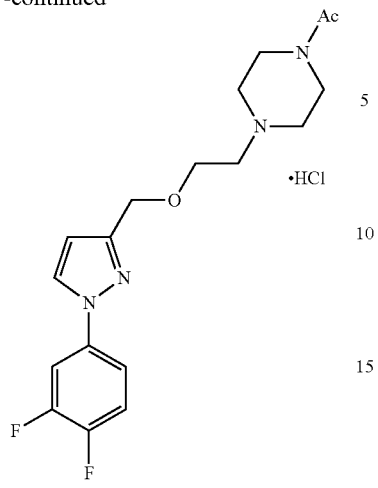

To a solution of 1-acetyl-4-({[1-(3,4-difluorophenyl)-1H-pyrazol-3-yl]methoxy}ethyhpiperazine (57.41 g, 157.55 mmol) in ethyl acetate (900 mL), HCl.Et$_2$O (2.0 M, 86.7 mL, 173.30 mmol) was added and the mixture was stirred at room temperature for 2 h. The mixture was evaporated to dryness, ethyl ether (300 mL) was added and evaporated again. This process was repeated two times with CH$_2$Cl$_2$ and ethyl ether. The solid thus obtained was triturated with hexane (400 mL) and filtered, washed with hexane (200 mL) and with ethyl ether/hexane (1:1, 100 mL). The solid was dried to give the title compound (61.2 g, 97% yield).

Figure 4:
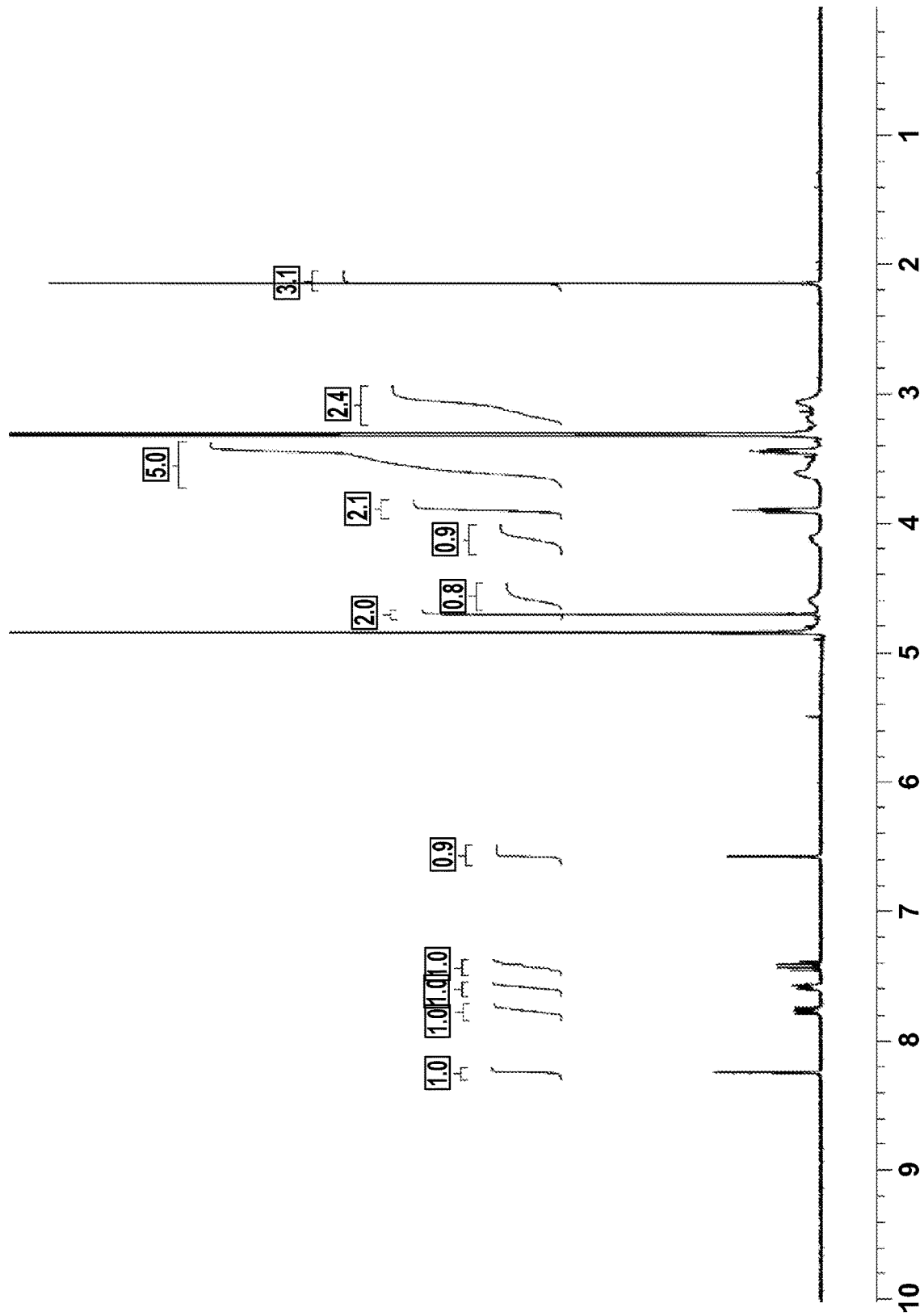
FIG. 4: $^1$H nuclear magnetic resonance of example 1.

RMN-$^1$H (CD$_3$OD, 400 MHz, □): 8.24 (d, J=2.7 Hz, 1H, ArH); 7.76 (ddd, J=11.7, 7.0, 2.7 Hz, 1H, ArH); 7.61-7.55 (m, 1H, ArH); 7.47-7.37(m, 1H, ArH); 6.58 (d, J=2.5 Hz, 1H, ArH); 4.71 (s, 2H, CH$_2$); 4.59 (sa, 1H, CH$_2$); 4.20-4.05 (m, 1H, CH$_2$); 3.96-3.85 (m, 2H, CH$_2$); 3.69-3.39 (m, 4 H, CH$_2$); 3.24-2.99 (m, 2H, CH$_2$); 2.14 (s, 3H, CH$_3$). (FIG. 4)

EM-ESI+m/z: 365 (M+1-HCl).

Figure 3:
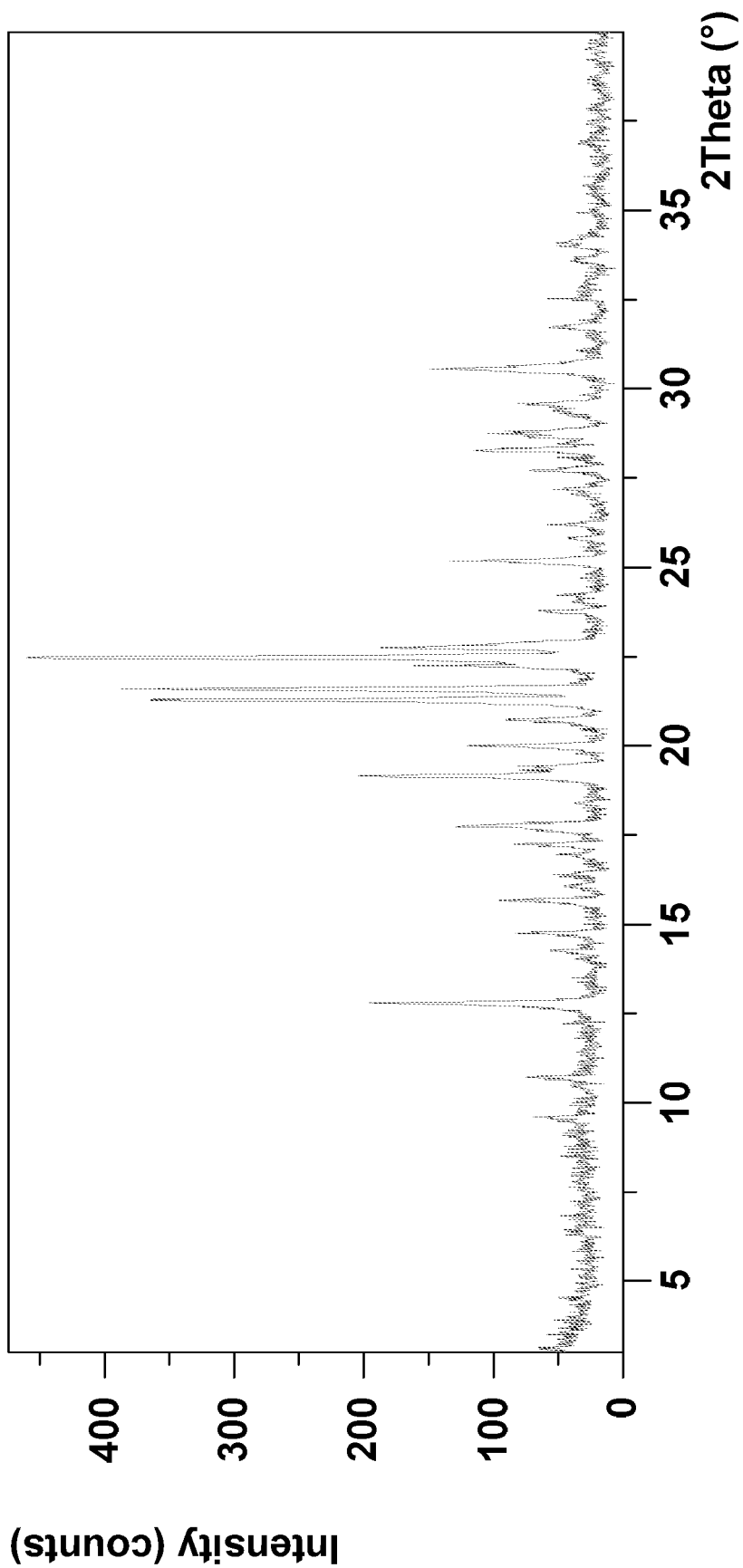
FIG. 3: X-Ray powder diffraction of example 1.
Figure 5:
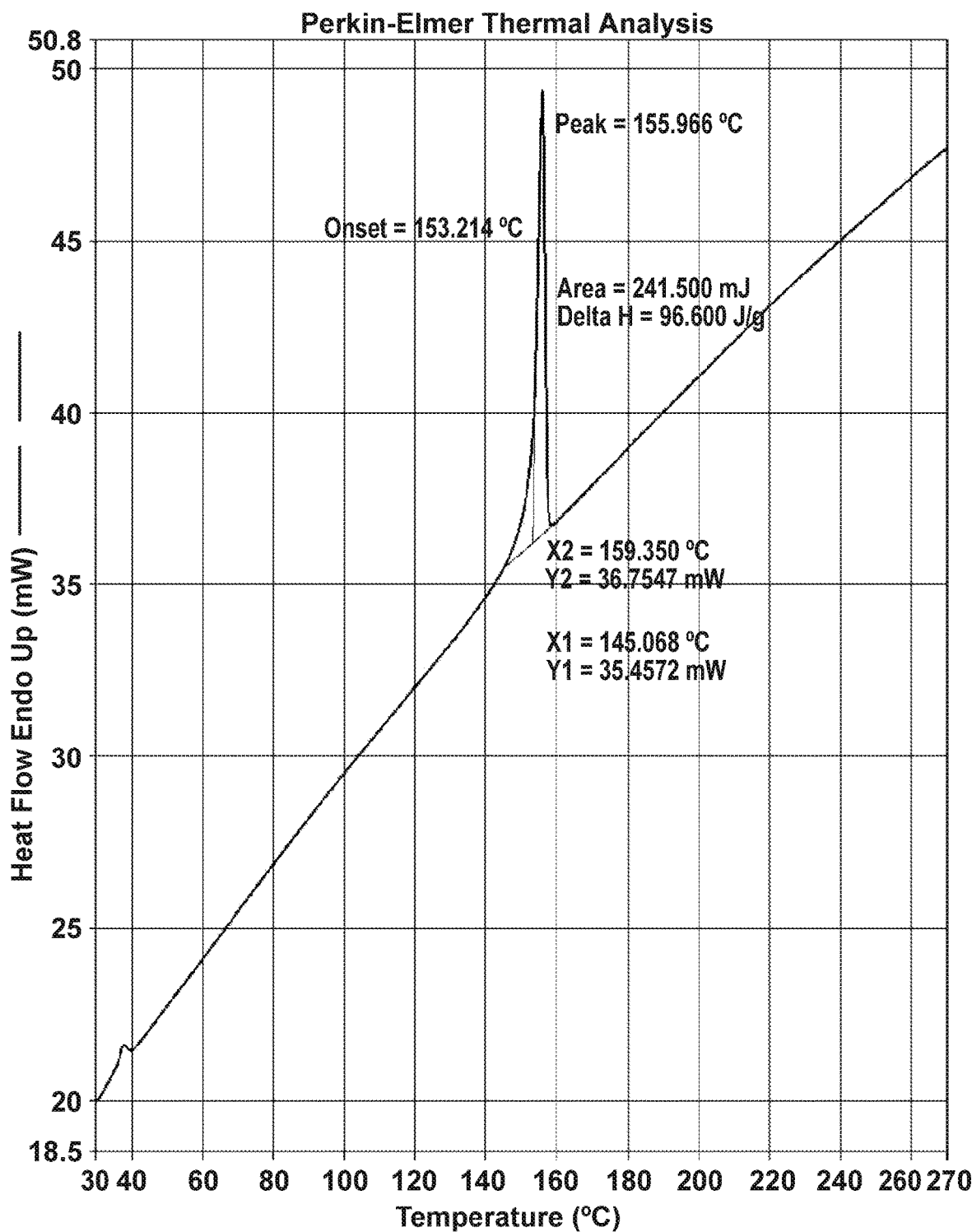
FIG. 5: Differential Scanning calorimetry (DSC) of example 1.

Example 1 was additionally characterized by X-Ray powder diffraction (FIG. 3) and by DSC (FIG. 5).

Example 2

Synthesis of 1-acetyl-4-({[1-(3,4-difluorophenyl)-1H-pyrazol-3-yl]methoxy}methyl)piperazine maleate

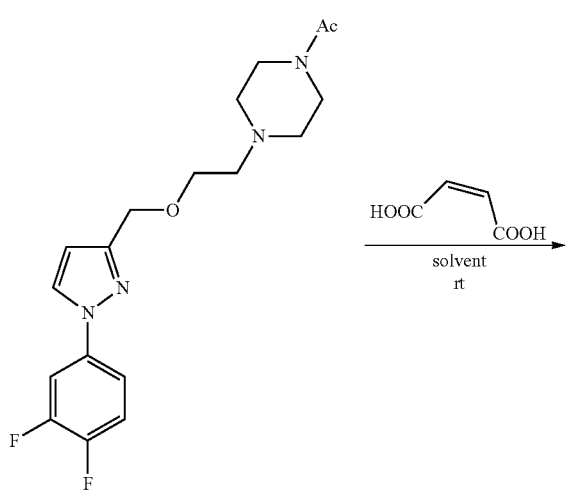

To a 2 mL Eppendorf tube containing 1-acetyl-4-({[1-(3,4-difluorophenyl)-1H-pyrazol-3-yl]methoxy}ethyl)piperazine (19 mg, 0.052 mmol) and maleic acid (6 mg, 0.052 mmol), 1 drop of ethanol and two stainless steel grinding balls were added before milling for 45 minutes at a rate of 30 Hz (3×15 minutes) with a Retsch Ball Mill MM400. After drying under vacuum at room temperature the title compound was obtained as an off white pasty solid to which ethyl ether (0.2 mL) was added before stirring at room temperature for 2 h. The resulting mixture was isolated by centrifugation (RT, 14000 rpm, 10 min). After drying under vacuum at room temperature the title compound was obtained as a solid with a good crystallinity (17 mg, 82% yield).

Figure 6:
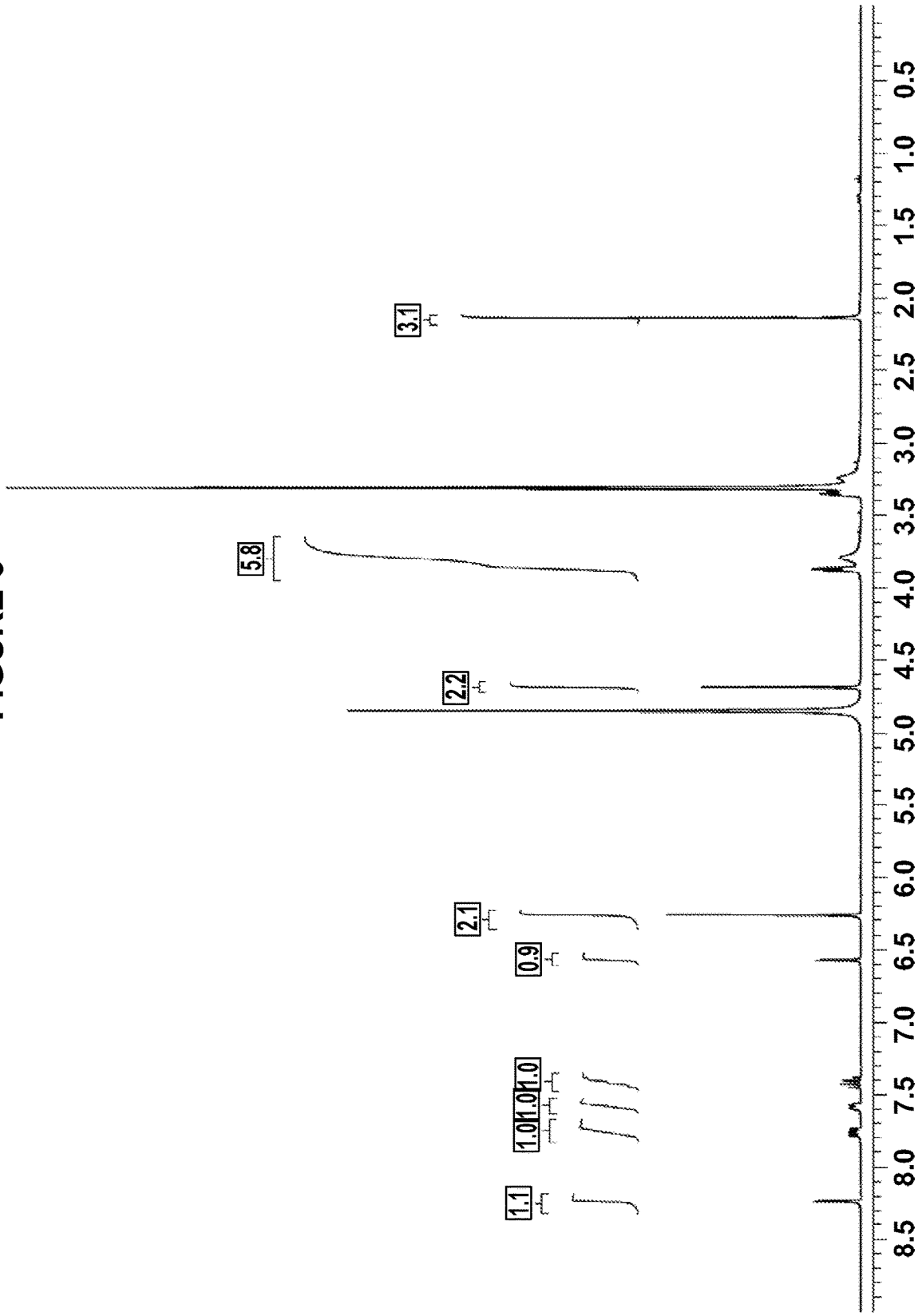
FIG. 6: $^1$H nuclear magnetic resonance of example 2.

RMN-$^1$H (CD$_3$OD, 400 MHz, □): 8.23 (d, J=2.7 Hz, 1H, ArH); 7.76 (ddd, J=11.1, 7.0, 2.7 Hz, 1H, ArH); 7.62-7.55 (m, 1H, ArH); 7.46-7.36 (m, 1H, ArH); 6.57 (d, J=2.7 Hz, 1H, ArH); 6.26 (s, 2 H, CH=); 4.69 (s, 2 H, CH$_2$); 3.92-3.84 (m, 2 H, CH$_2$); 3.84-3.70 (m, 4 H, CH$_2$); 3.39-3.15 (m, 6 H, CH$_2$); 2.13 (s, 3H, CH$_3$). (FIG. 6)

Figure 7:
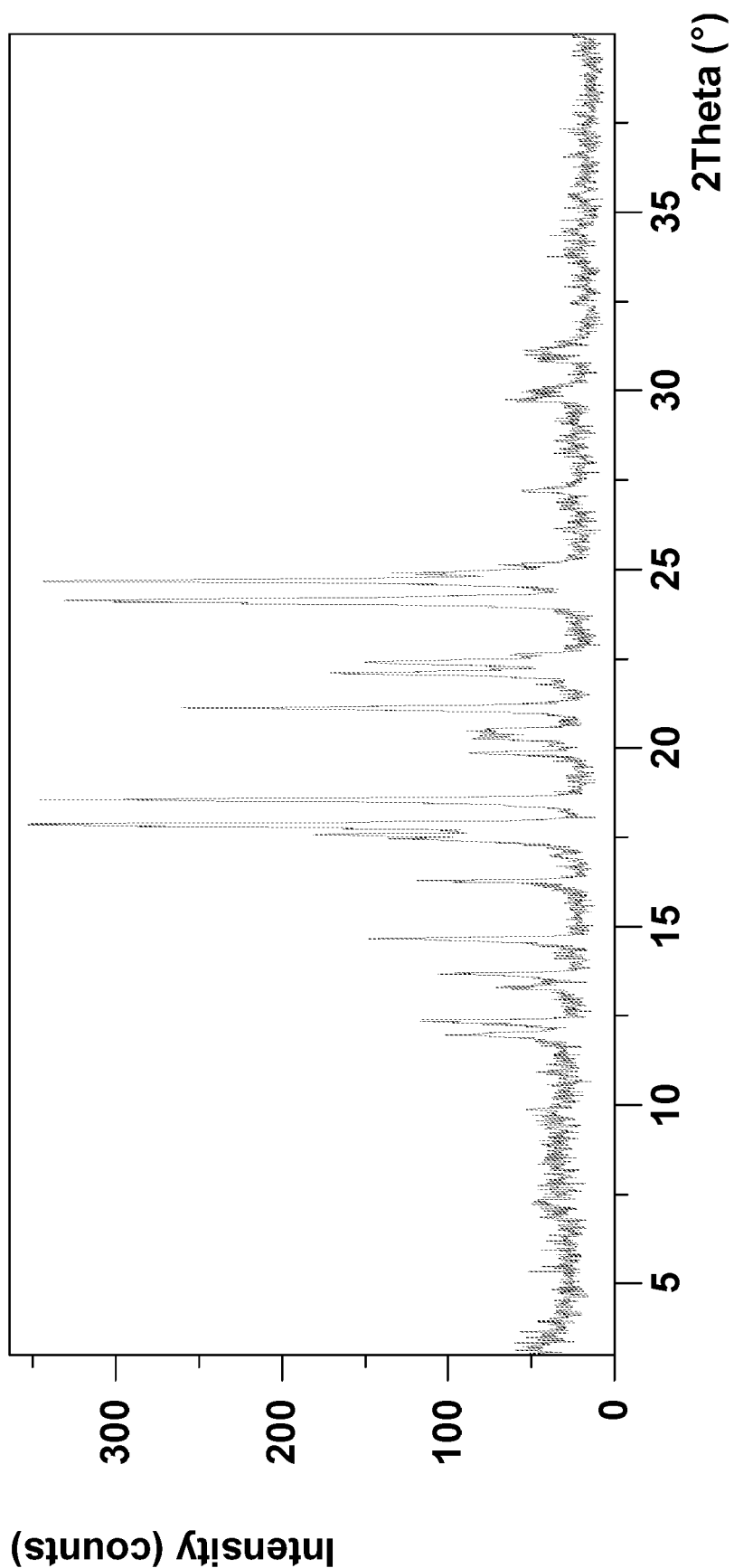
FIG. 7: X-Ray powder diffraction of example 2.
Figure 8:
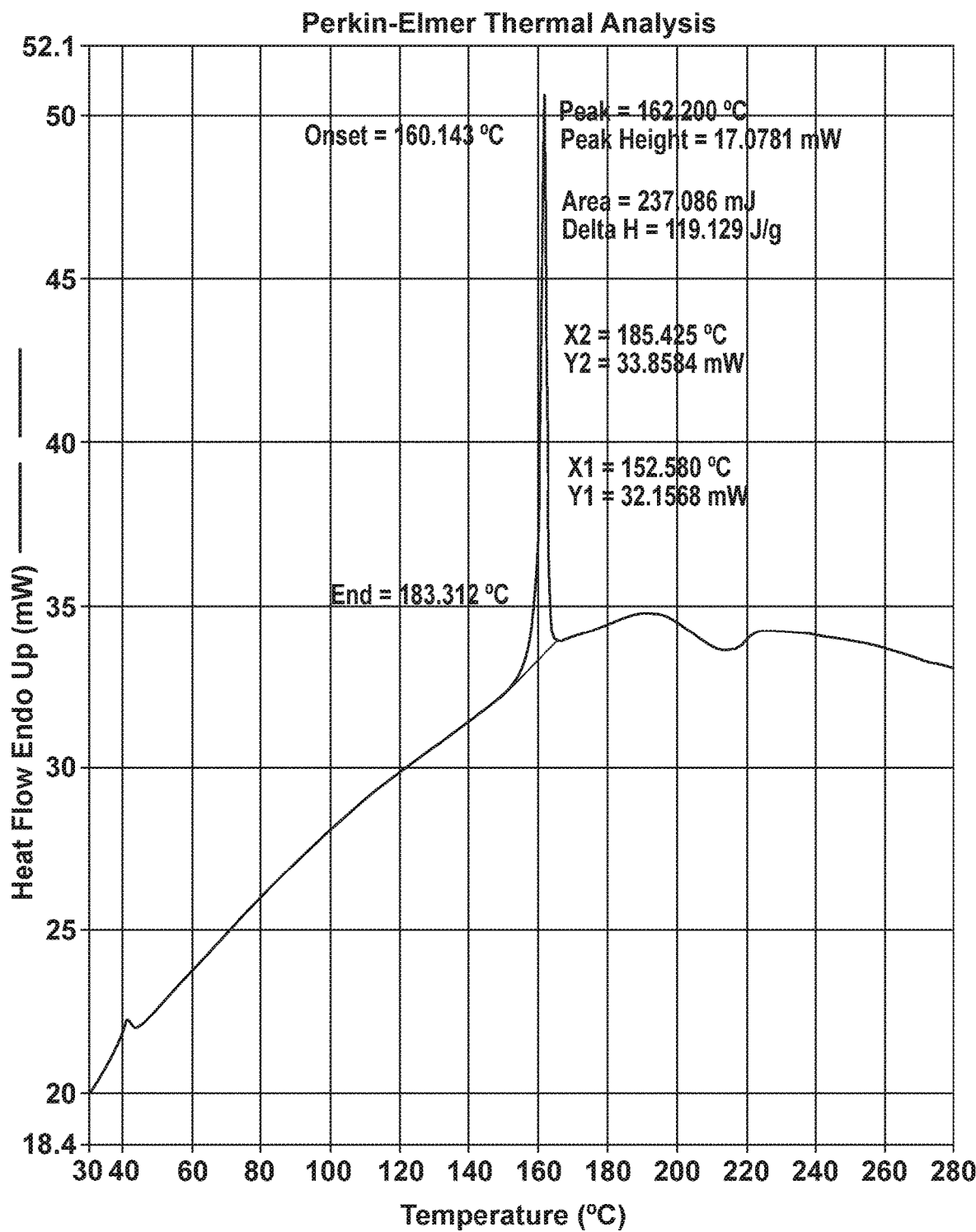
FIG. 8: Differential Scanning calorimetry (DSC) of example 2.

Example 2 was additionally characterized characterized by X-Ray powder diffraction (FIG. 7) and by DSC (FIG. 8).

Alternatively, the compound of Example 2 can be prepared using the following procedure:

To an assay tube equipped with magnetic stirrer containing a turbid solution of 1-acetyl-4-({[1-(3,4-difluorophenyl)-1H-pyrazol-3-yl]methoxy}ethyl)piperazine (109.1 mg, 0.2994 mmol) in tert-butyl methyl ether (1.1 mL) at 45° C., maleic acid (35.2 mg, 0.303 mmol) was added. The resulting paste was vigorously stirred 1 h at 45° C. affording a suspension of a crystalline solid. Then the resultant suspension was cooled down to room temperature and stirred for 2 h. The solid was filtered with a sintered funnel (porosity 3) and washed with tert-butyl methyl ether (1×2 vol.). After drying under vacuum at room temperature the title compound was obtained as a crystalline solid (109 mg, 76% yield).

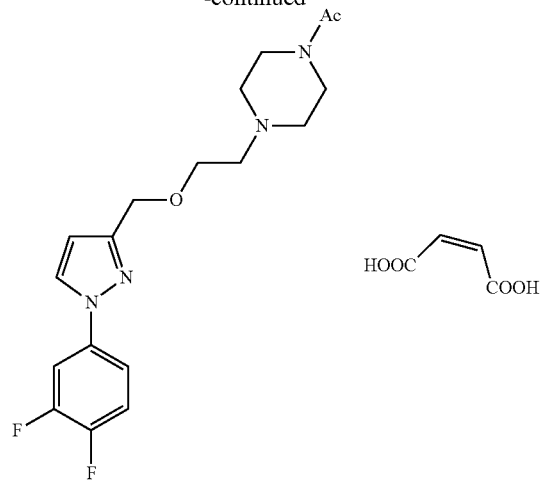

Example 3

Synthesis of 1-acetyl-4-({[1-(3,4-difluorophenyl)-1H-pyrazol-3-yl]methoxy}methyl)piperazine fumarate

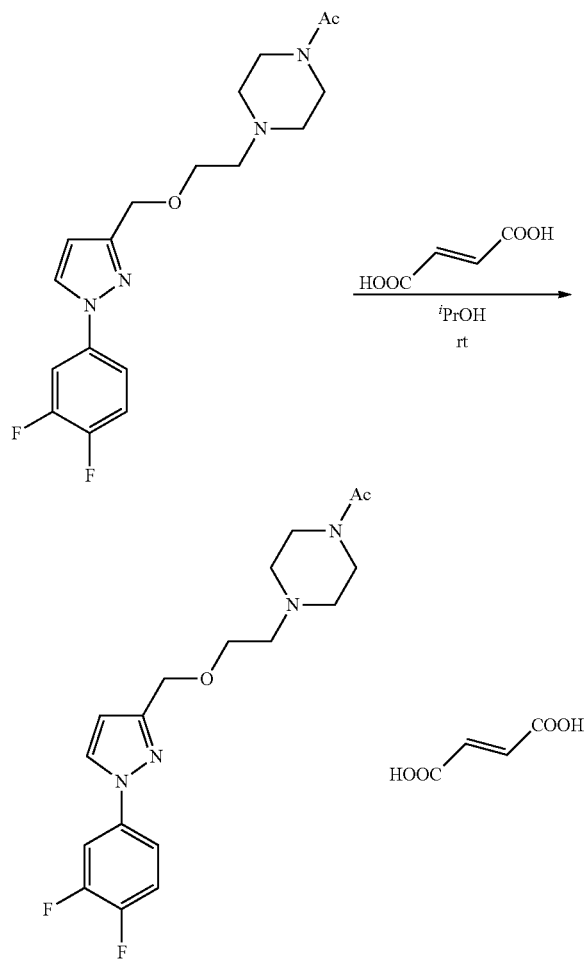

To an assay tube equipped with magnetic stirrer containing 1-acetyl-4-({[1-(3,4-difluorophenyl)-1H-pyrazol-3-yl]methoxy}ethyl)piperazine (35 mg, 0.1 mmol) and fumaric acid (11.7 mg, 0.1 mmol, 1 eq.), isopropanol (0.35 mL) was added at room temperature. After 3 h of stirring at room temperature, the resultant suspension was filtered and washed with isopropanol (1×1.5 vol.). After drying under vacuum at room temperature, the title compound was obtained as a crystalline solid (33 mg, 68% yield).

Figure 9:
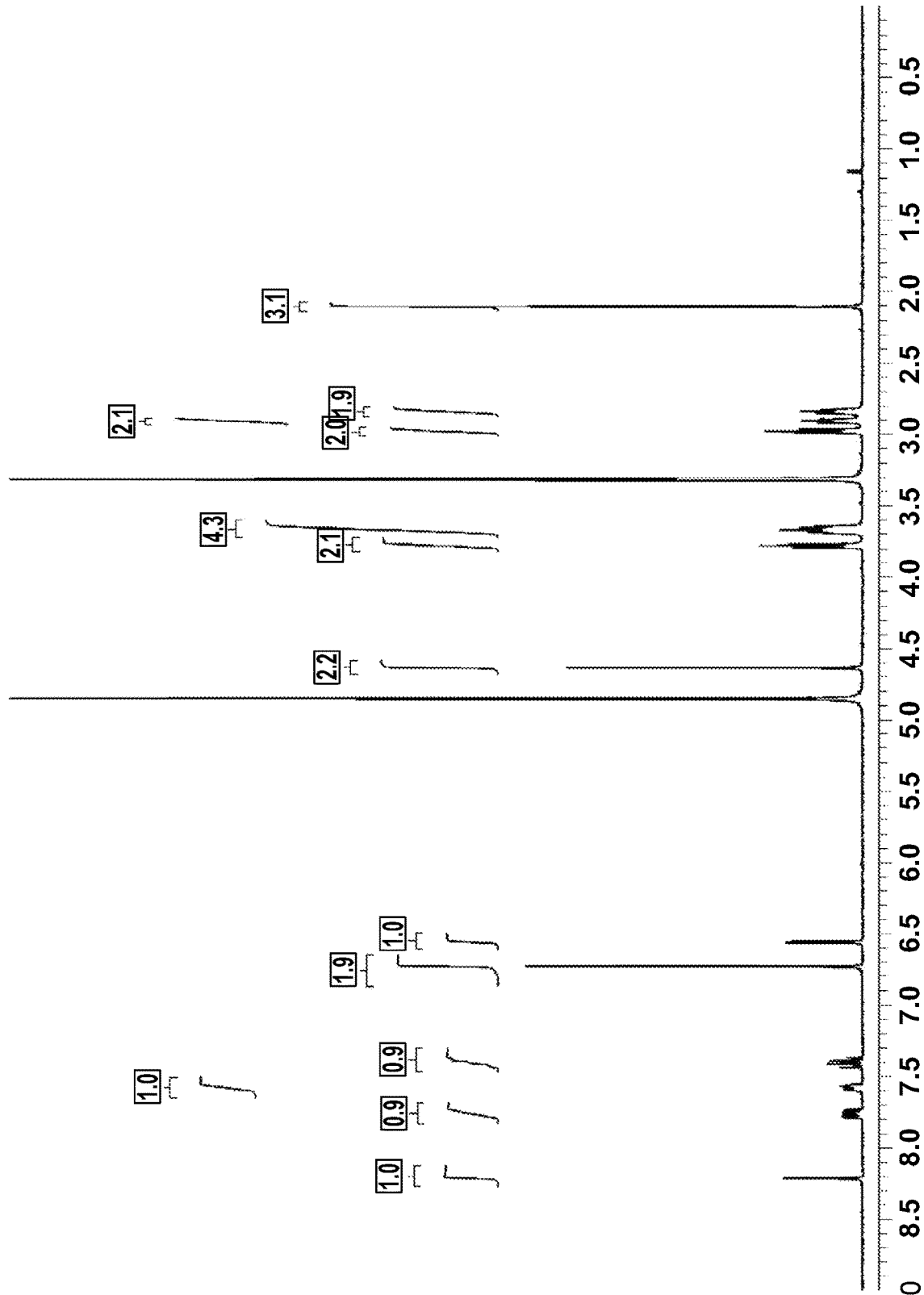
FIG. 9: $^1$H nuclear magnetic resonance of example 3.

RMN-$^1$H (CD$_3$OD, 400 MHz, □): 8.21 (d, J=2.7 Hz, 1H, ArH); 7.75 (ddd, J=11.1, 7.0, 2.7 Hz, 1H, ArH); 7.61-7.54 (m, 1H, ArH); 7.45-7.35 (m, 1H, ArH); 6.73 (s, 2 H, CH═); 6.55 (d, J=2.7 Hz, 1H, ArH); 4.64 (s, 2 H, CH$_2$); 3.81-3.74 (m, 2 H, CH$_2$); 3.73-3.61 (m, 4 H, CH$_2$); 3.01-2.94 (m, 2 H, CH$_2$); 2.94-2.87 (m, 2 H, CH$_2$); 2.87-2.79 (m, 2 H, CH$_2$); 2.11 (s, 3H, CH$_3$). (FIG. 9)

Figure 10:
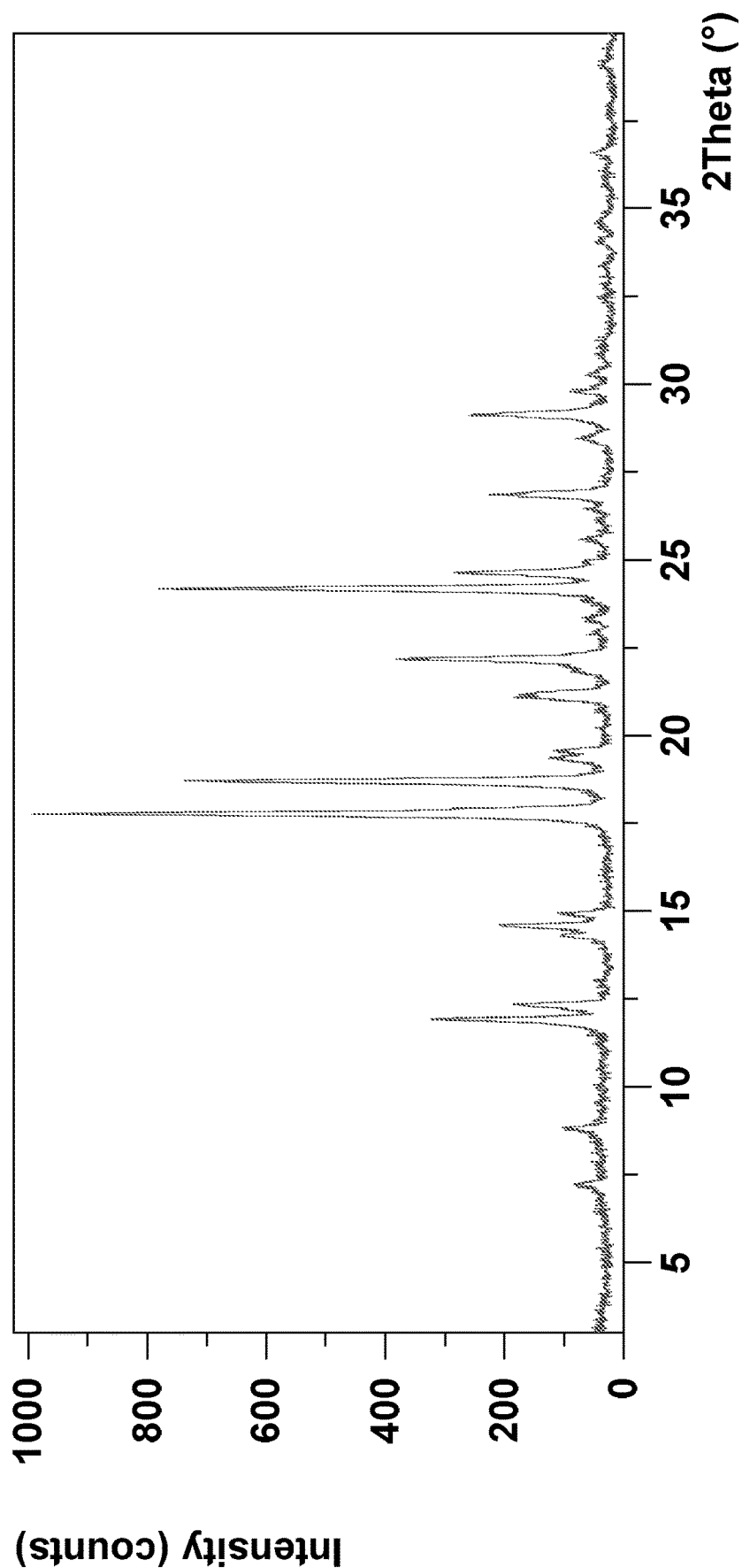
FIG. 10: X-Ray powder diffraction of example 3.
Figure 11:
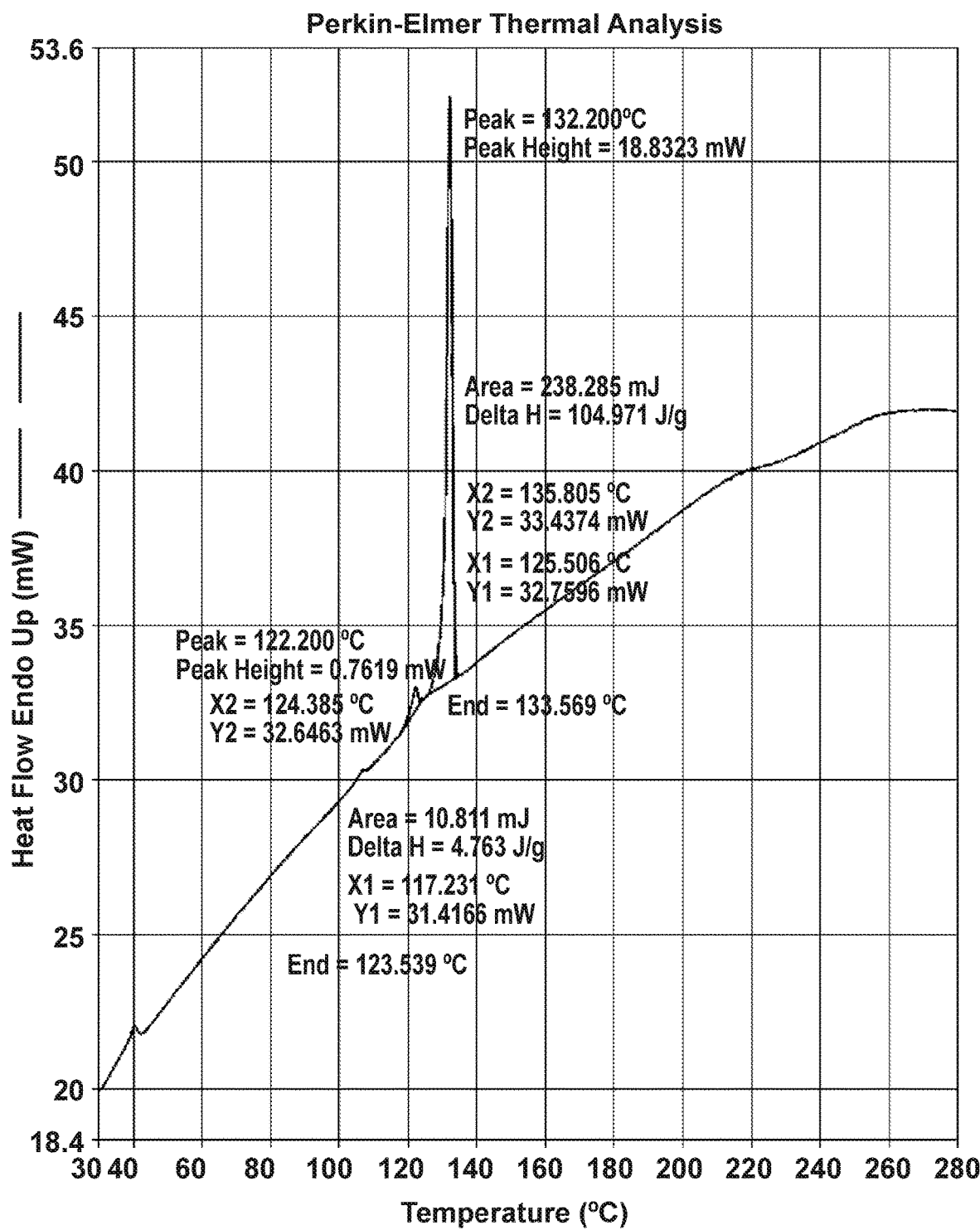
FIG. 11: Differential Scanning calorimetry (DSC) of example 3.

Example 3 was additionally characterized characterized by X-Ray powder diffraction (FIG. 10) and by DSC (FIG. 11).

Example 4

Synthesis of 1-acetyl-4-({[1-(3,4-difluorophenyl)-1H-pyrazol-3-yl]methoxy}methyl)piperazine malonate

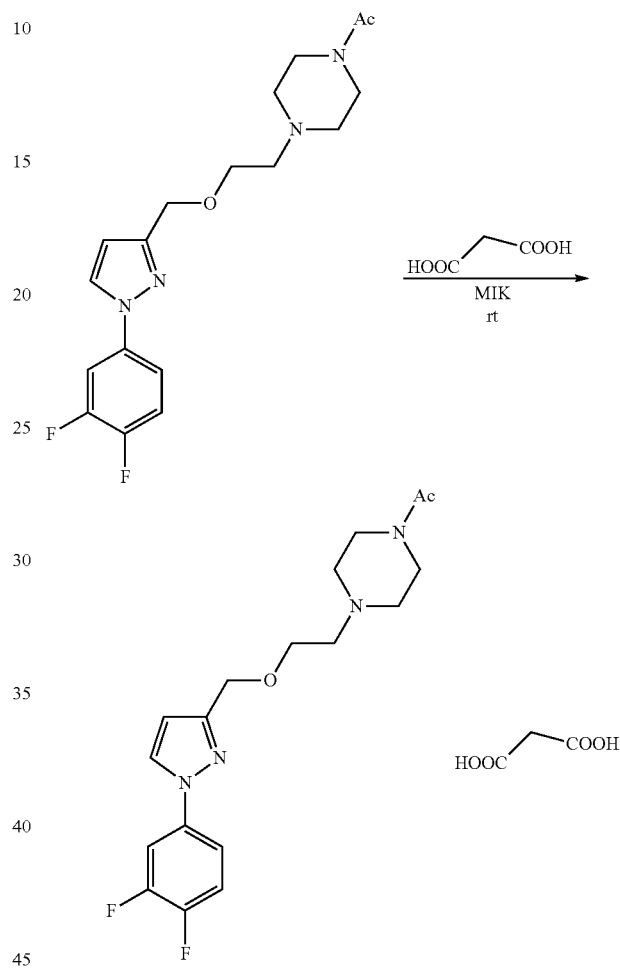

To an assay tube equipped with magnetic stirrer containing 1-acetyl-4-({[1-(3,4-difluorophenyl)-1H-pyrazol-3-yl]methoxy}ethyl)piperazine (35 mg, 0.1 mmol) and fumaric acid (10 mg, 0.1 mmol), methyl isobutyl ketone (0.3 mL) at room temperature was added. After 3 h the resultant suspension was filtered and washed with methyl isobutyl ketone (1×1.5 vol.). After drying under vacuum at room temperature, the title compound was obtained as a solid (35 mg, 75% yield).

Figure 12:
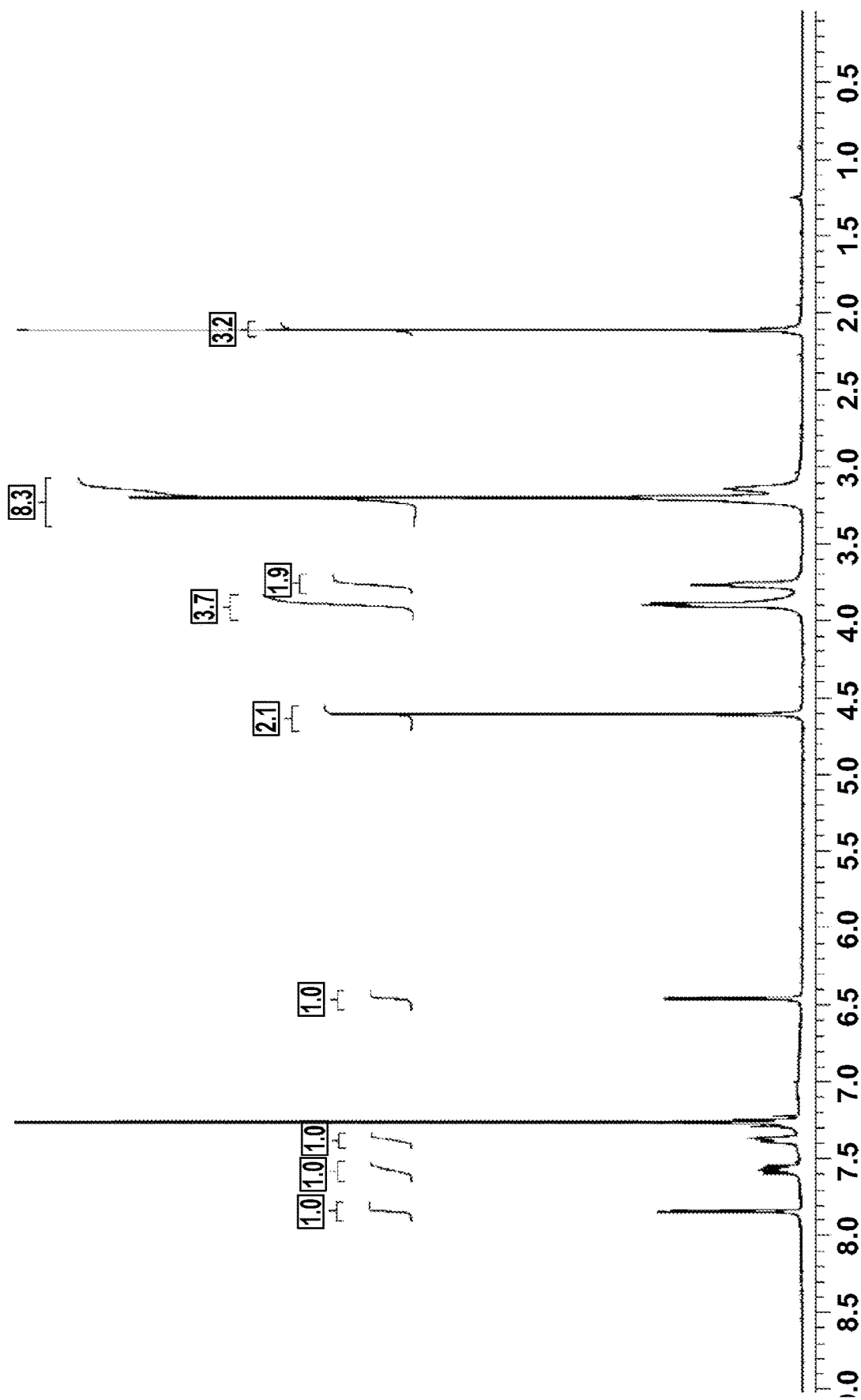
FIG. 12: $^1$H nuclear magnetic resonance of example 4.

RMN-$^1$H (CDCl$_3$, 400 MHz, □): 7.84 (d, J=2.7 Hz, 1H, ArH); 7.57 (ddd, J=11.1, 7.0, 2.7 Hz, 1H, ArH); 7.41-7.34 (m, 1H, ArH); 7.30-7.21 (m, 1H, ArH); 6.45 (d, J=2.7 Hz, 1H, ArH); 4.61 (s, 2 H, CH$_2$); 3.96-3.83 (m, 4 H, CH$_2$); 3.81-3.73 (m, 2 H, CH$_2$); 3.29-3.17 (m, 6 H, CH$_2$); 3.17-3.09 (m, 2 H, CH$_2$); 2.11 (s, 3H, CH$_3$). (FIG. 12)

Figure 13:
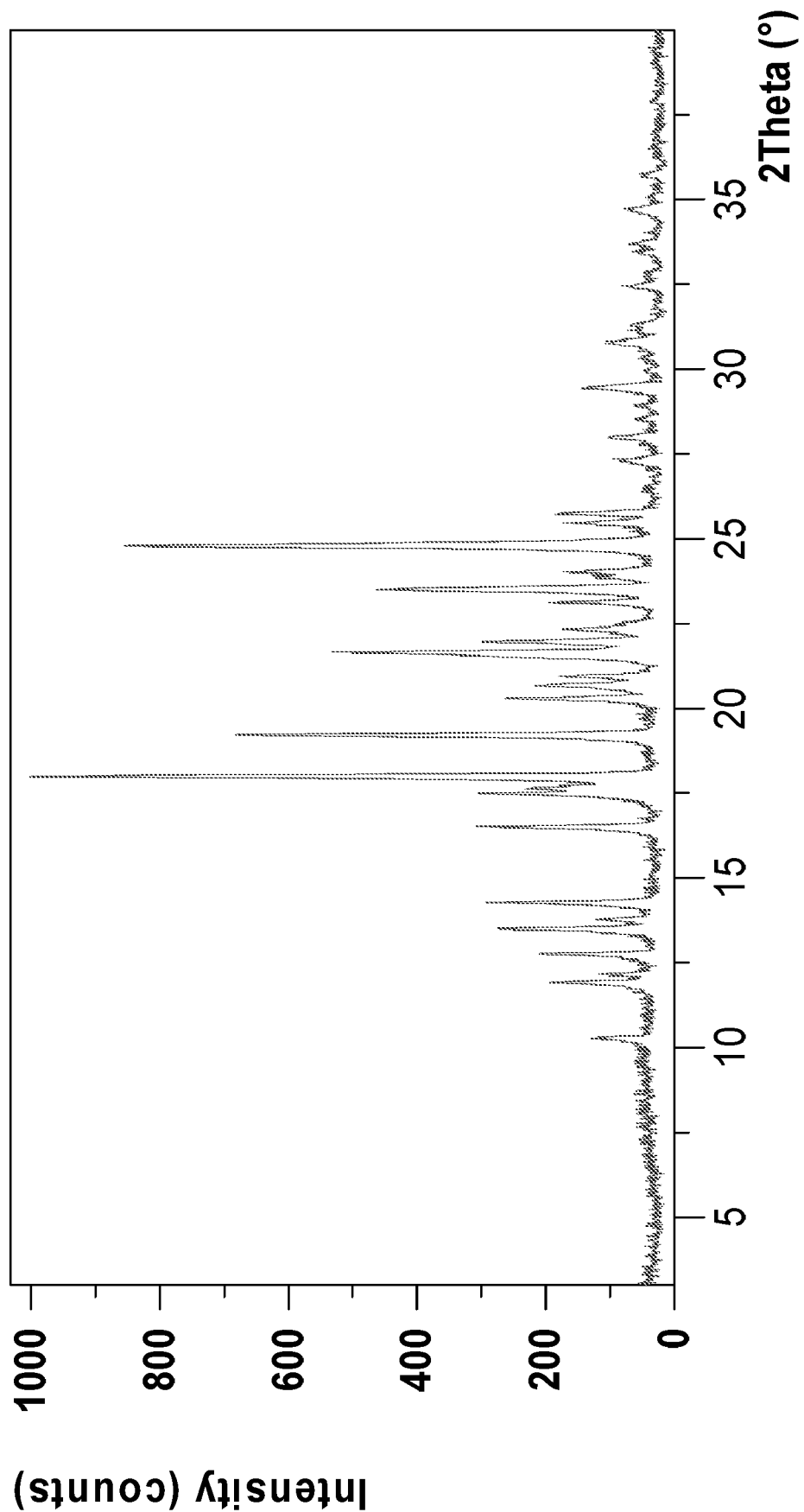
FIG. 13: X-Ray powder diffraction of example 4.
Figure 14:
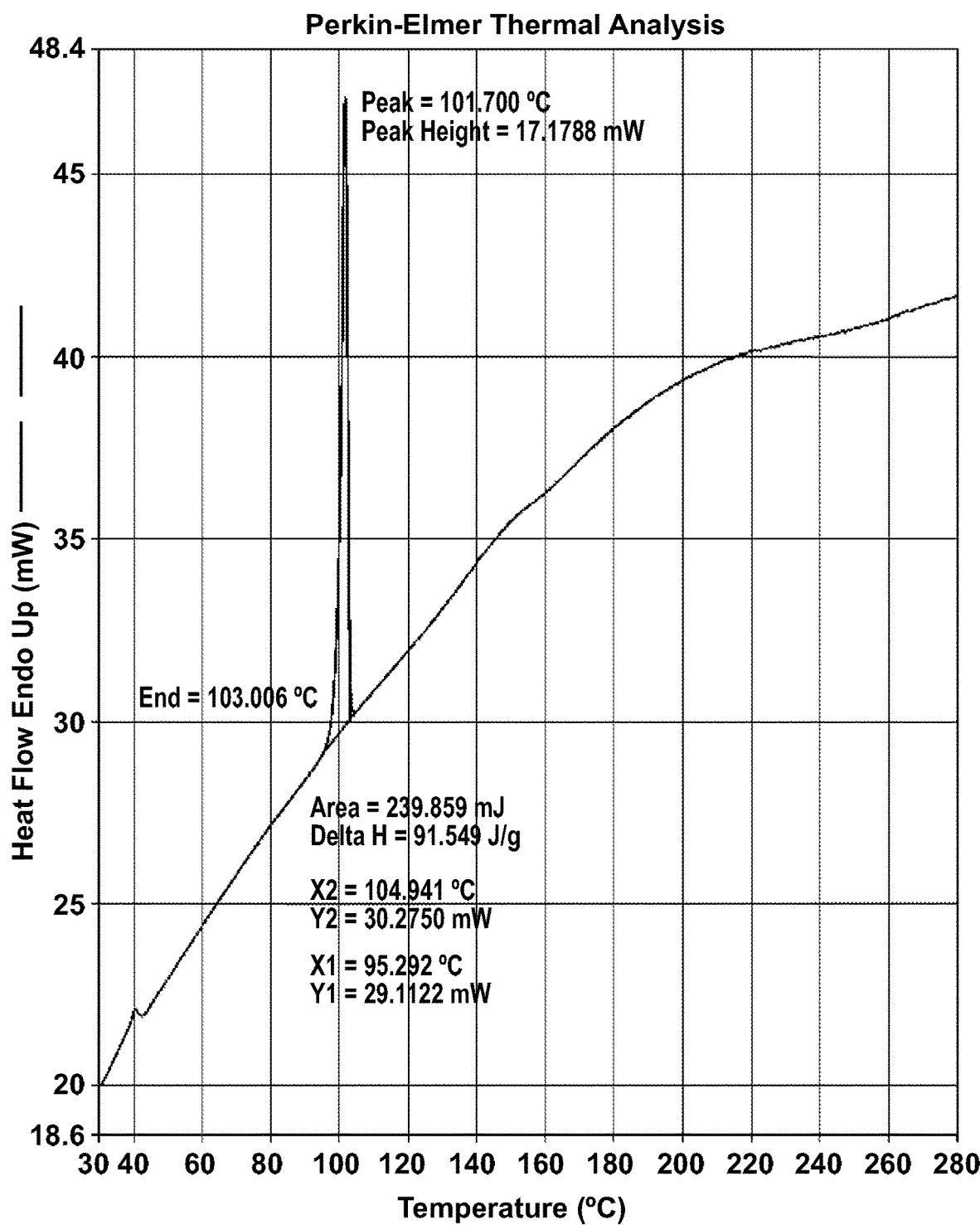
FIG. 14: Differential Scanning calorimetry (DSC) of example 4.

Example 4 was additionally characterized characterized by X-Ray powder diffraction (FIG. 13) and by DSC (FIG. 14).

Example 5

Synthesis of 1-acetyl-4-({[1-(3,4-difluorophenyl)-1H-pyrazol-3-yl]methoxy}methyl)piperazine oxalate

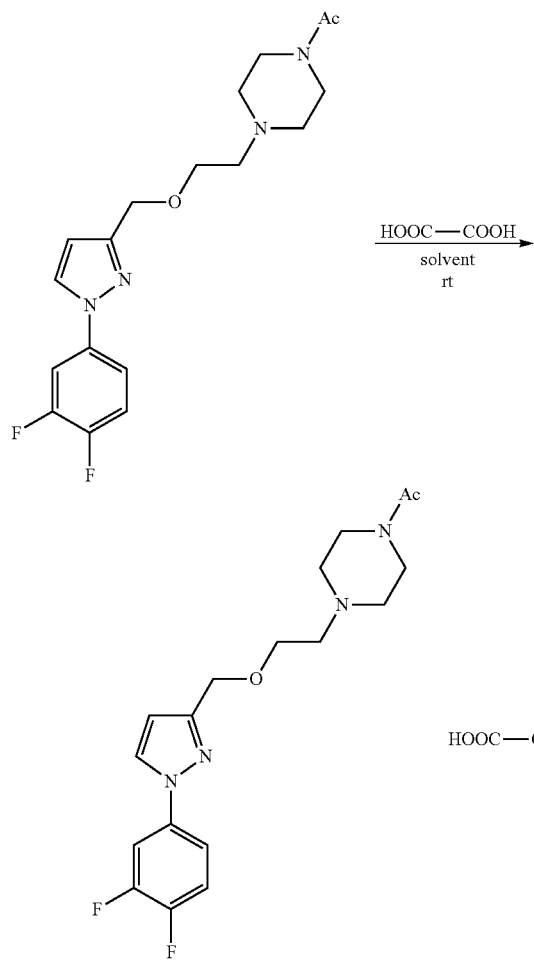

To a 2 mL Eppendorf tube containing 1-acetyl-4-({[1-(3,4-difluorophenyl)-1H-pyrazol-3-yl]methoxy}ethyl)piperazine (25 mg, 0.068 mmol) and oxalic acid (6.9 mg, 0.077 mmol), 1 drop of tert-butyl methyl ether and two stainless steel grinding balls were added before milling 45 minutes at a rate of 30 Hz (3×15 minutes) with a Retsch Ball Mill MM400. After drying under vacuum at room temperature, the title compound was obtained as a crystalline solid in a quantitative yield.

Figure 15:
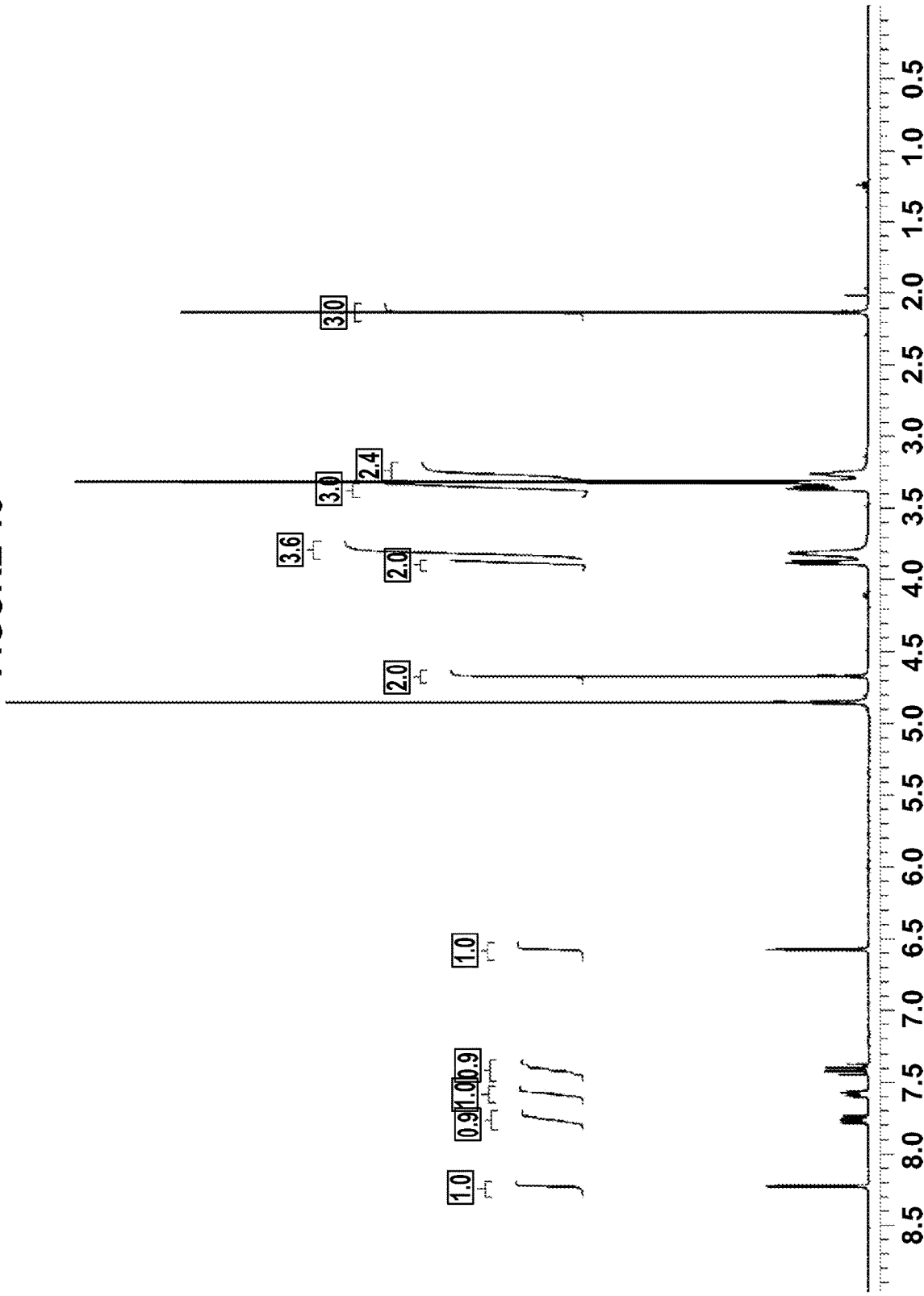
FIG. 15: $^1$H nuclear magnetic resonance of example 5.

RMN-$^1$H (CD$_3$OD, 400 MHz, □): 8.22 (d, J=2.7 Hz, 1H, ArH); 7.76 (ddd, J=11.7, 7.0, 2.7 Hz, 1H, ArH); 7.61-7.55 (m, 1H, ArH); 7.45-7.36 (m, 1H, ArH); 6.57 (d, J=2.7 Hz, 1H, ArH); 4.67 (s, 2H, CH$_2$); 3.92-3.85 (m, 2H, CH$_2$); 3.82-3.75 (m, 4H, CH$_2$); 3.38-3.29 (m, 4H, CH$_2$); 3.29-3.21 (m, 2H, CH$_2$); 2.13 (s, 3H, CH$_3$). (FIG. 15)

Figure 16:
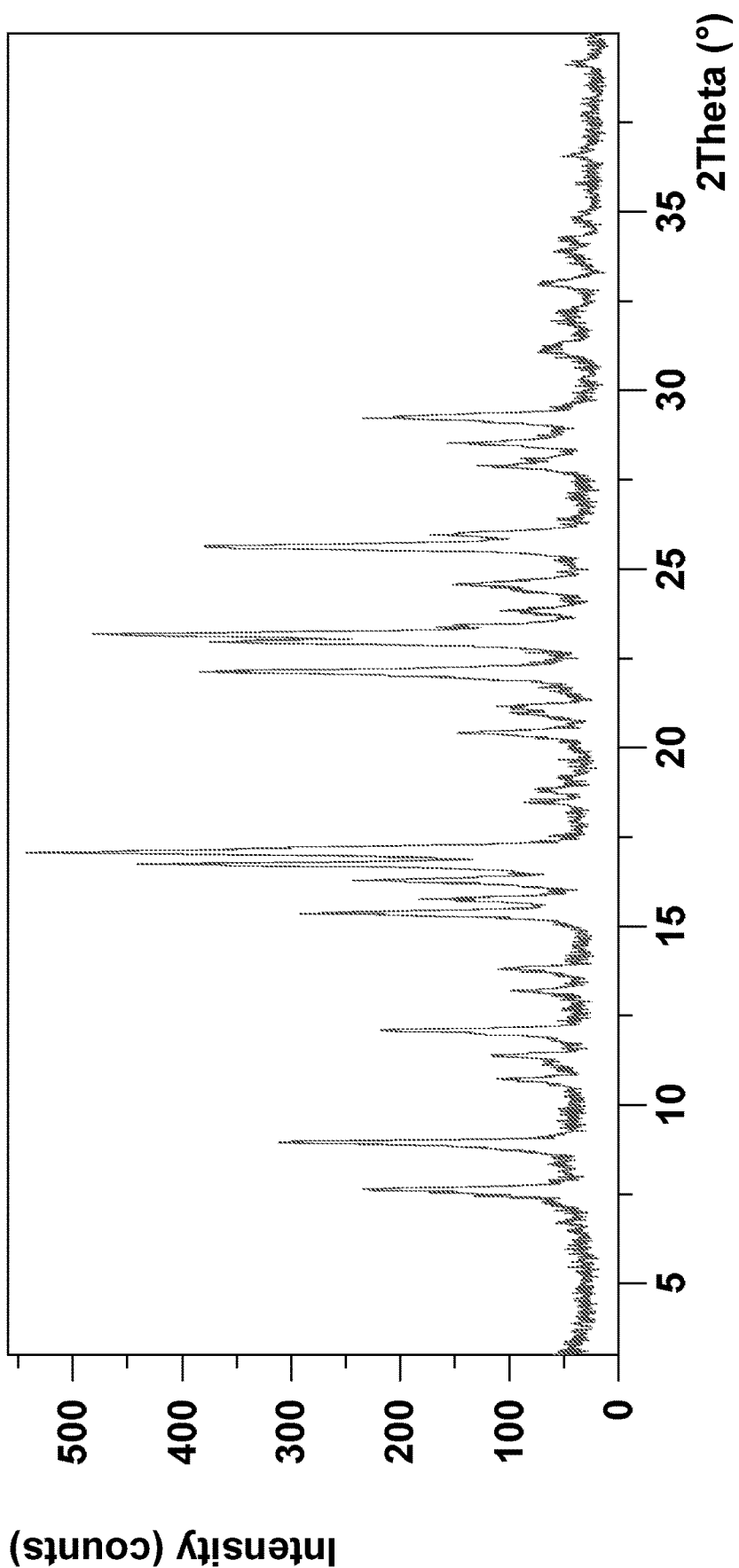
FIG. 16: X-Ray powder diffraction of example 5.
Figure 17:
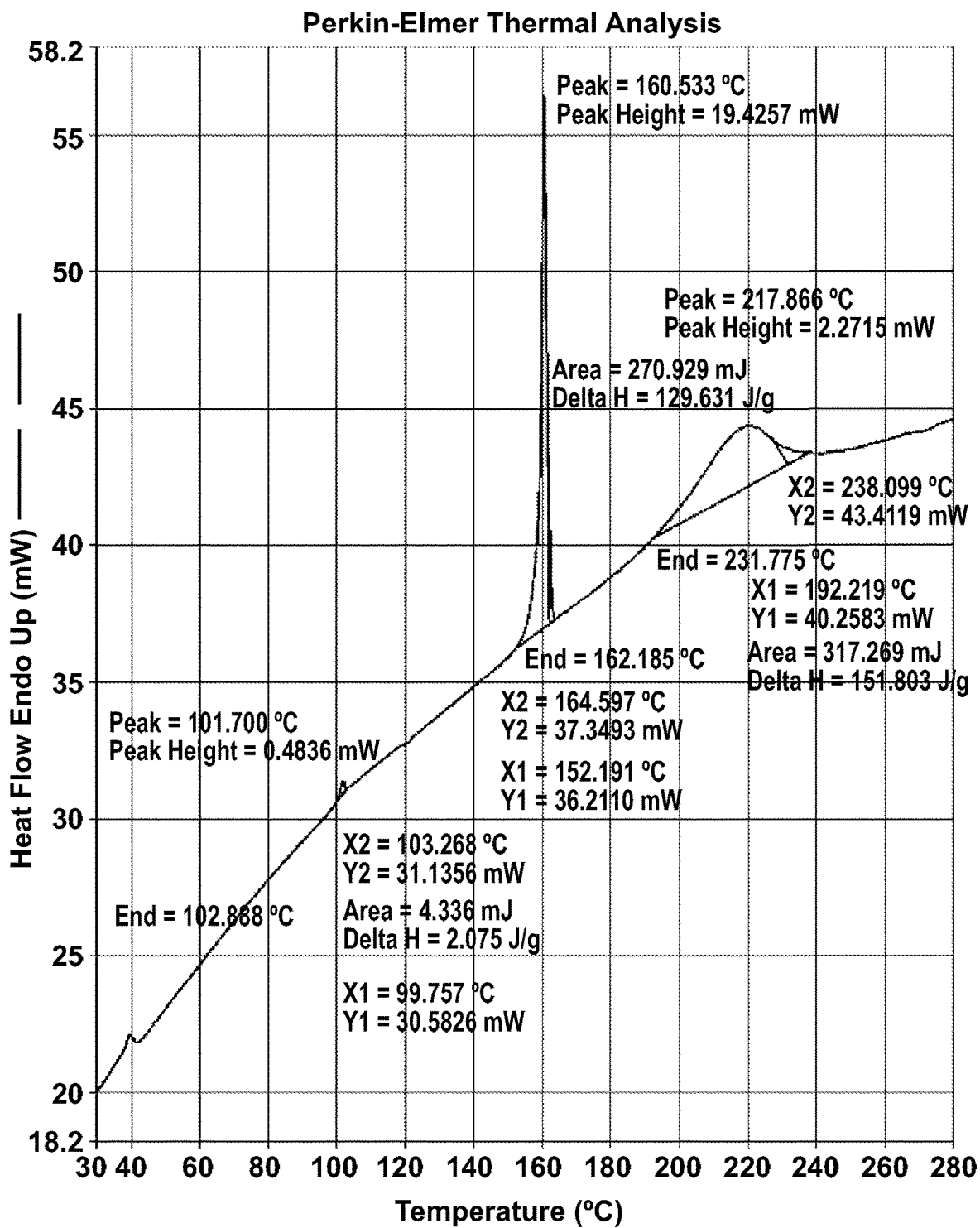
FIG. 17: Differential Scanning calorimetry (DSC) of example 5.

Example 5 was additionally characterized characterized by X-Ray powder diffraction (FIG. 16) and by DSC (FIG. 17).

Alternatively, the compound of Example 5 can be prepared using the following procedure:

To an Eppendorf tube equipped with magnetic stirrer containing a solution of 1-acetyl-4-({[1-(3,4-difluorophenyl)-1H-pyrazol-3-yl]methoxy}ethyl)piperazine (30 mg, 0.082 mmol) in ethyl acetate (0.3 mL), oxalic acid (7.5 mg, 0.083 mmol) was added at room temperature. After 3 h of stirring a precipitate was observed and the resultant suspension was centrifuged to isolate the solid. Ethyl acetate (0.2 mL) was added to the solid and centrifuged again. The recovered solid was dried under vacuum at room temperature to afford the title compound as a crystalline solid (37 mg, 99% yield).

Example 6

Synthesis of 1-acetyl-4-({[1-(3,4-difluorophenyl)-1H-pyrazol-3-yl]methoxy}methyl)piperazine succinate

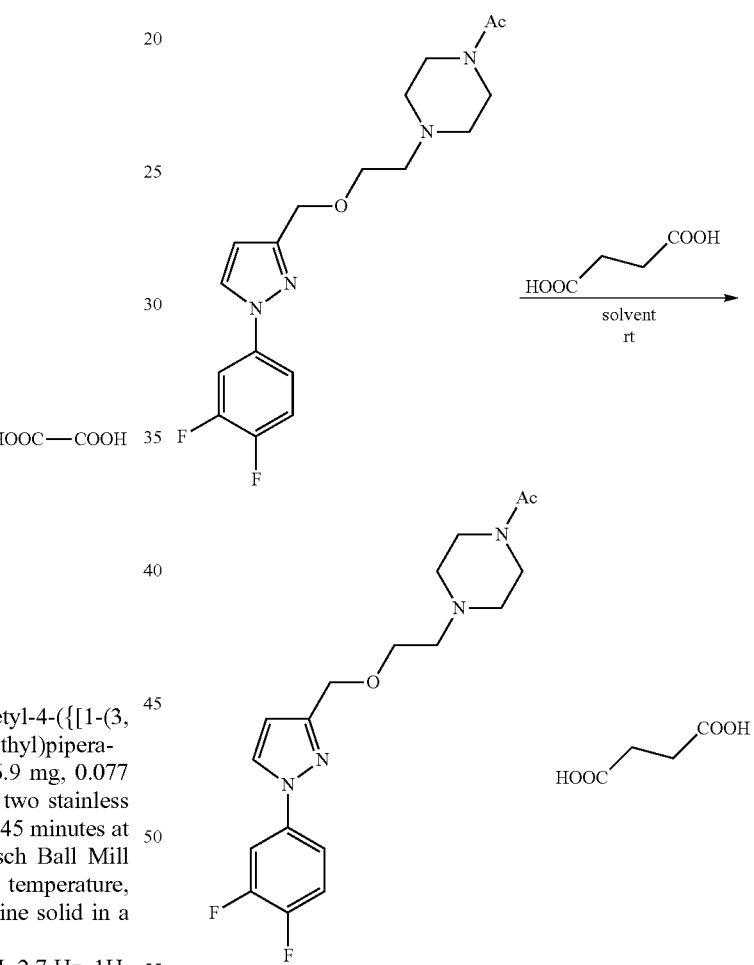

To a 2 mL Eppendorf tube containing 1-acetyl-4-({[1-(3,4-difluorophenyl)-1H-pyrazol-3-yl]methoxy}ethyl)piperazine (24.6 mg, 0.067 mmol) and succinic acid (10 mg, 0.084 mmol), 1 drop of tert-butyl methyl ether and two stainless steel grinding balls were added before milling 45 minutes at a rate of 30 Hz (3×15 minutes) with a Retsch Ball Mill MM400. The resulting solid was dried under vacuum at room temperature to afford an amorphous solid (25 mg) to which isobutyl methyl ketone (0.2 mL) was added. The mixture was stirred at room temperature for 16 h and the resulting suspension was centrifuged. The solid thus obtained was dried at room temperature under vacuum to give the title compound as a solid (15 mg, 46% yield).

Figure 18:
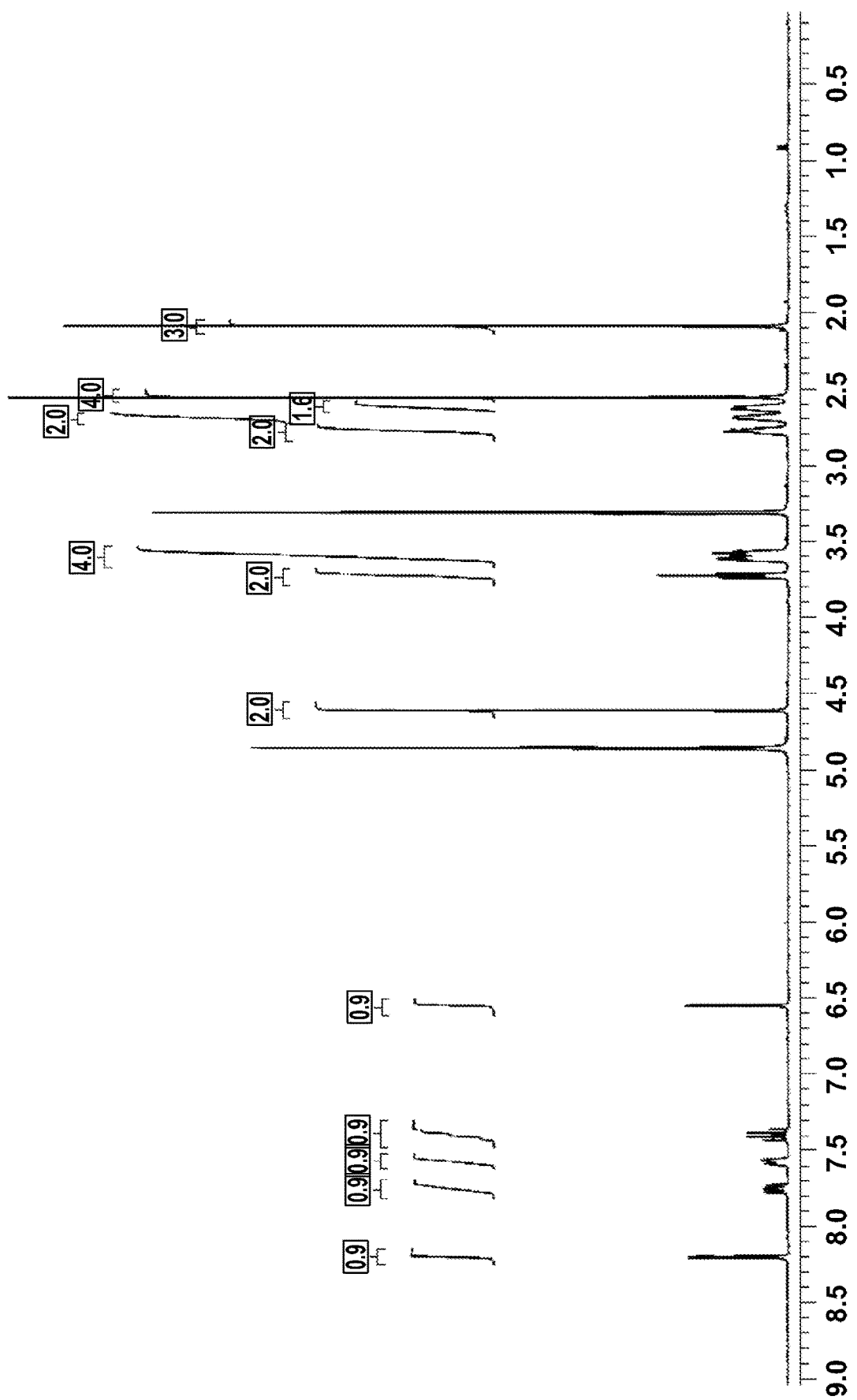
FIG. 18: $^1$H nuclear magnetic resonance of example 6.

RMN-¹H (CD$_3$OD, 400 MHz, □): 8.20 (d, J=2.7 Hz, 1H, ArH); 7.75 (ddd, J=11.7, 7.0, 2.7 Hz, 1H, ArH); 7.60-7.54 (m, 1H, ArH); 7.44-7.35 (m, 1H, ArH); 6.55 (d, J=2.7 Hz, 1H, ArH); 4.61 (s, 2H, CH$_2$); 3.72 (t, J=5.5, 2H, CH$_2$); 3.67-3.53 (m, 4H, CH$_2$); 2.84-2.73 (m, 2H, CH$_2$); 2.73-2.65 (m, 2H, CH$_2$); 2.65-2.58 (m, 2H, CH$_2$); 2.56 (s, 4H); 2.0.9 (s, 3H, CH$_3$). (FIG. 18).

Figure 19:
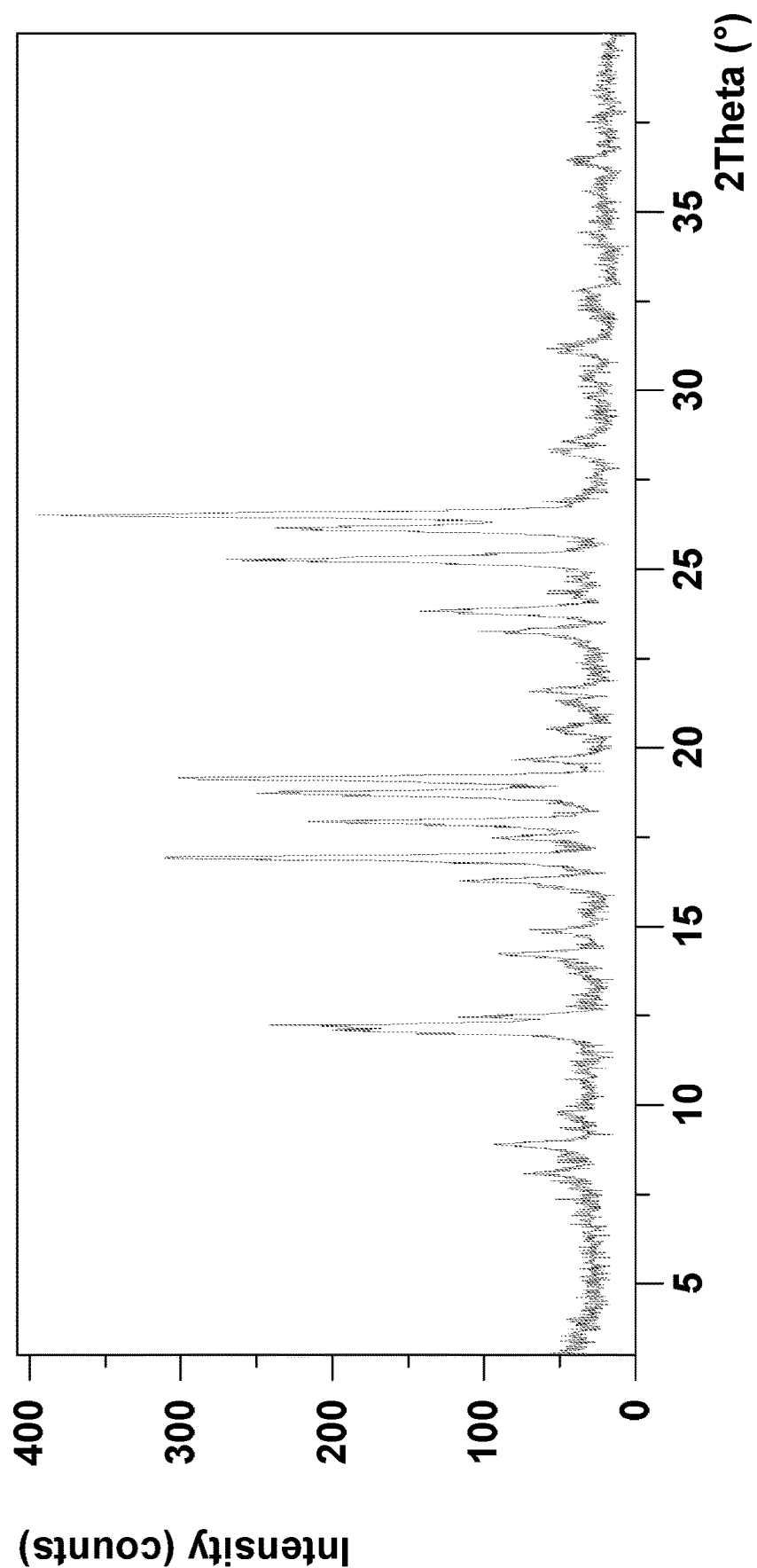
FIG. 19: X-Ray powder diffraction of example 6.
Figure 20:
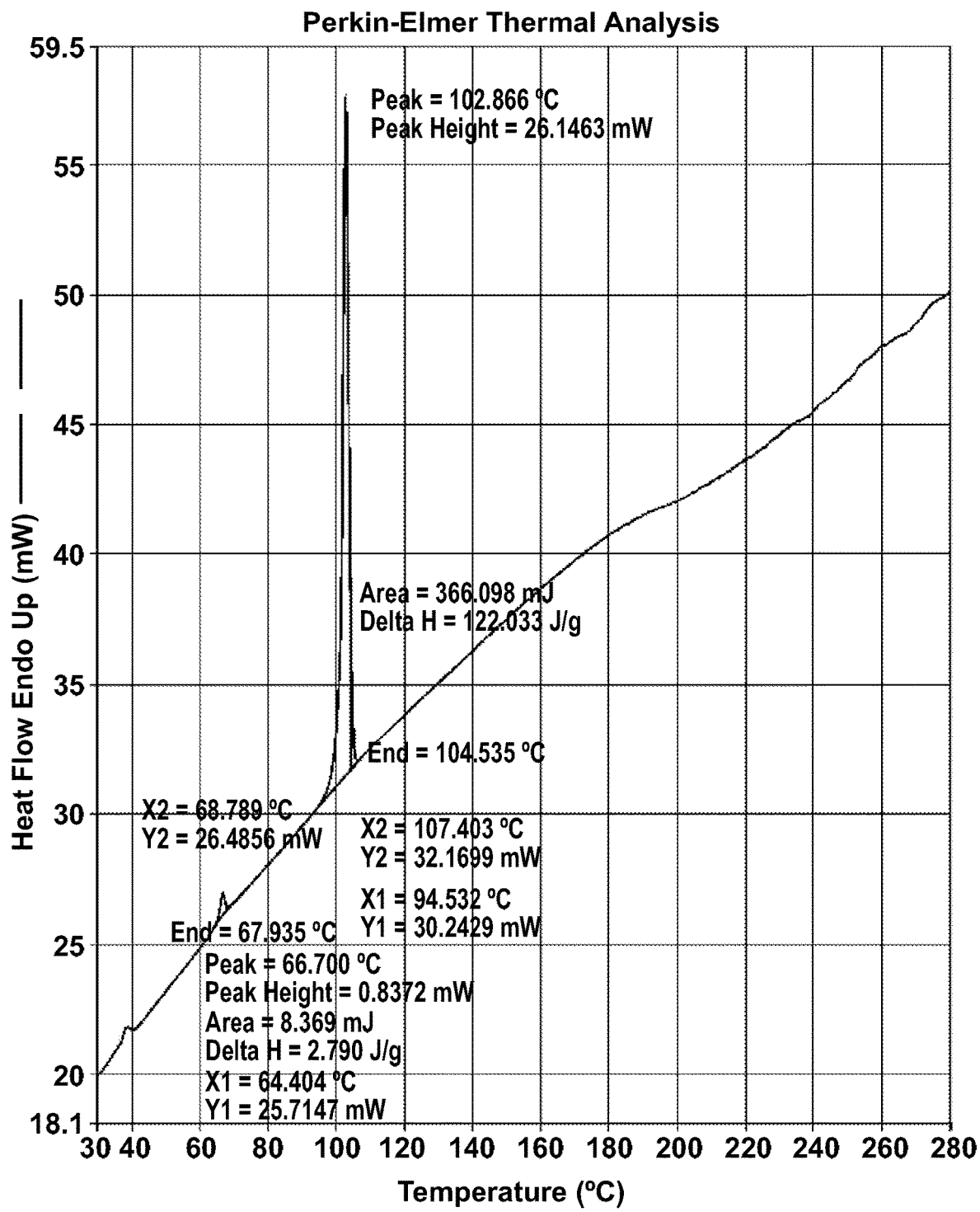
FIG. 20: Differential Scanning calorimetry (DSC) of example 6.

Example 6 was additionally characterized characterized by X-Ray powder diffraction (FIG. 19) and by DSC (FIG. 20).

Alternatively, the compound of Example 6 can be prepared using the following procedure:

To an Eppendorf tube equipped with magnetic stirrer containing a solution of 1-acetyl-4-({[1-(3,4-difluorophenyl)-1H-pyrazol-3-yl]methoxy}ethyl)piperazine (30 mg, 0.082 mmol) in ethyl acetate (0.3 mL), succinic acid (10 mg, 0.084 mmol) was added at room temperature. After one night of stirring at room temperature a precipitate was observed. The resultant suspension was centrifuged (25° C., 14000 rpm, 10 min) to isolate the solid. Tert-butyl methyl ether (0.2 mL) was added and the mixture centrifuged again (25° C., 14000 rpm, 10 min). The recovered solid was dried under vacuum at room temperature to afford the title compound as a solid (36 mg, 91% yield).

Example 7

Synthesis of 1-acetyl-4-({[1-(3,4-difluorophenyl)-1H-pyrazol-3-yl]methoxy}methyl)piperazine hydrobromide

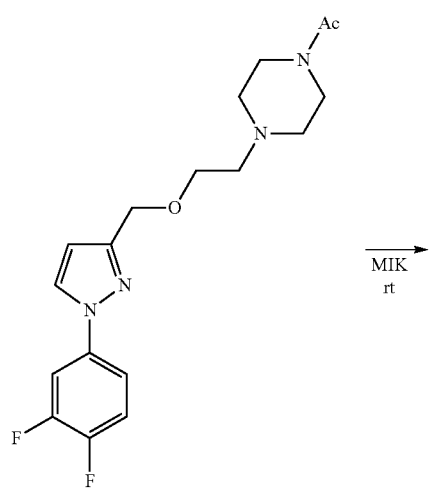

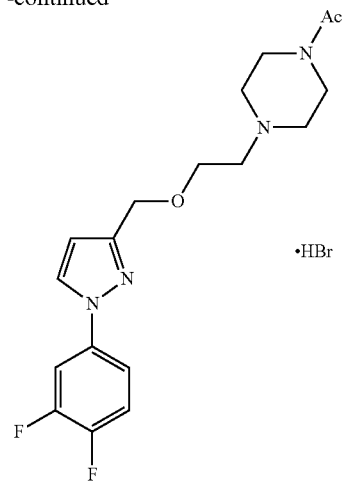

To an Eppendorf tube equipped with magnetic stirrer containing a solution of 1-acetyl-4-({[1-(3,4-difluorophenyl)-1H-pyrazol-3-yl]methoxy}ethyl)piperazine (15 mg, 0.041 mmol) in isobutyl methyl ketone (0.3 mL), a solution of HBr in IPA (50 µl of a solution prepared from 50 µl 48% HBr aqueous and 0.5 mL IPA, 0.04 mmol) was added at room temperature. After 2 h of stirring a precipitate was observed. The resultant suspension was centrifuged and the solid thus obtained was dried under vacuum at room temperature to afford the title compound as a crystalline solid (14 mg, 79% yield).

Figure 21:
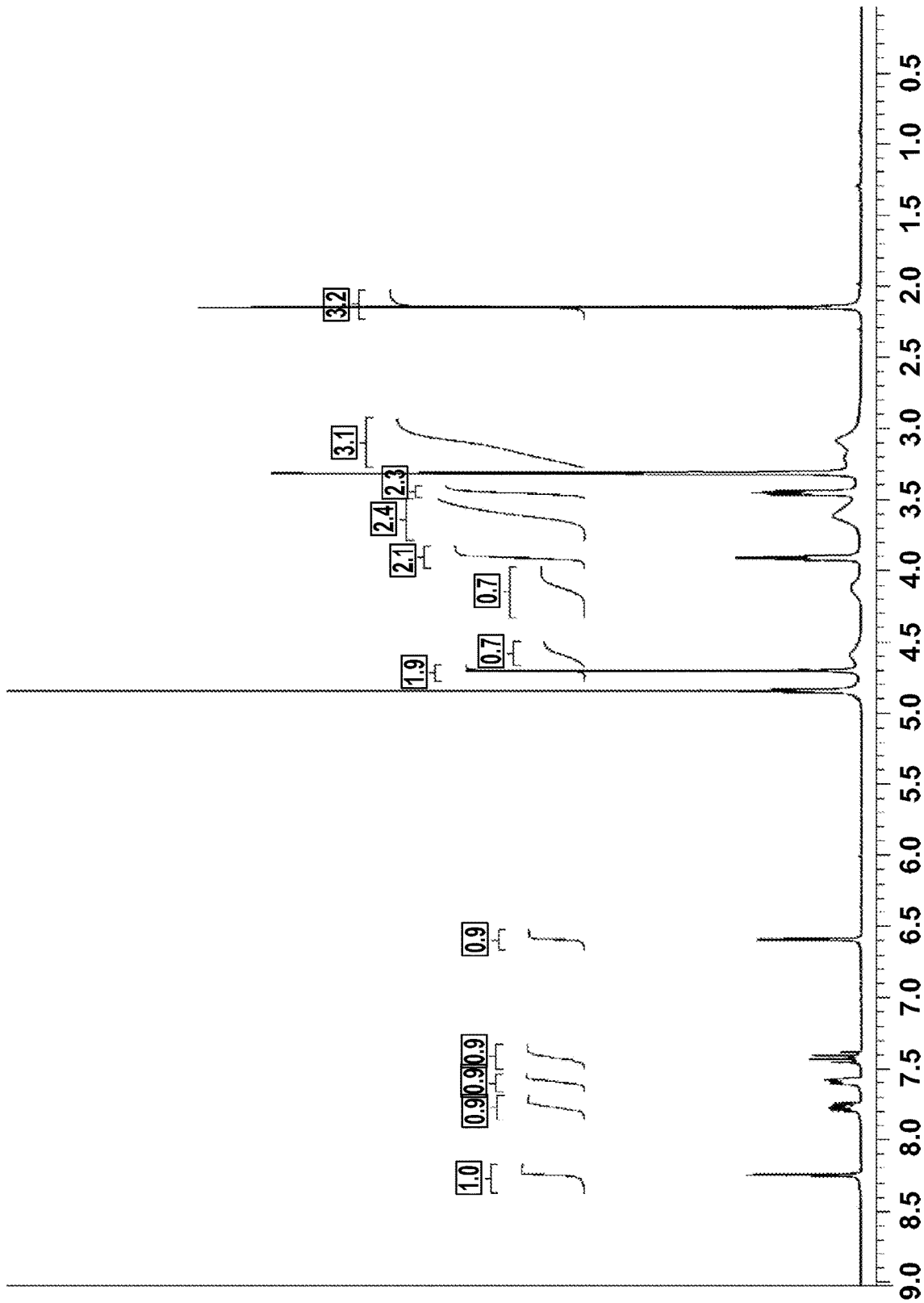
FIG. 21: $^1$H nuclear magnetic resonance of example 7.

RMN-¹H (CD$_3$OD, 400 MHz, □): 8.24 (d, J=2.7 Hz, 1H, ArH); 7.76 (ddd, J=11.7, 7.0, 2.7 Hz, 1H, ArH); 7.62-7.55 (m, 1H, ArH); 7.47-7.37(m, 1H, ArH); 6.58 (d, J=2.5 Hz, 1H, ArH); 4.70 (s, 2H, CH$_2$); 4.59 (sa, 1H, CH$_2$); 4.11 (sa, 1H, CH$_2$); 3.96-3.85 (m, 2H, CH$_2$); 3.74-3.49 (m, 2 H, CH$_2$); 3.49-3.41 (m, 2H, CH$_2$); 3.26-2.98 (m, 2H, CH$_2$); 2.14 (s, 3H, CH$_3$). (FIG. 21).

Figure 22:
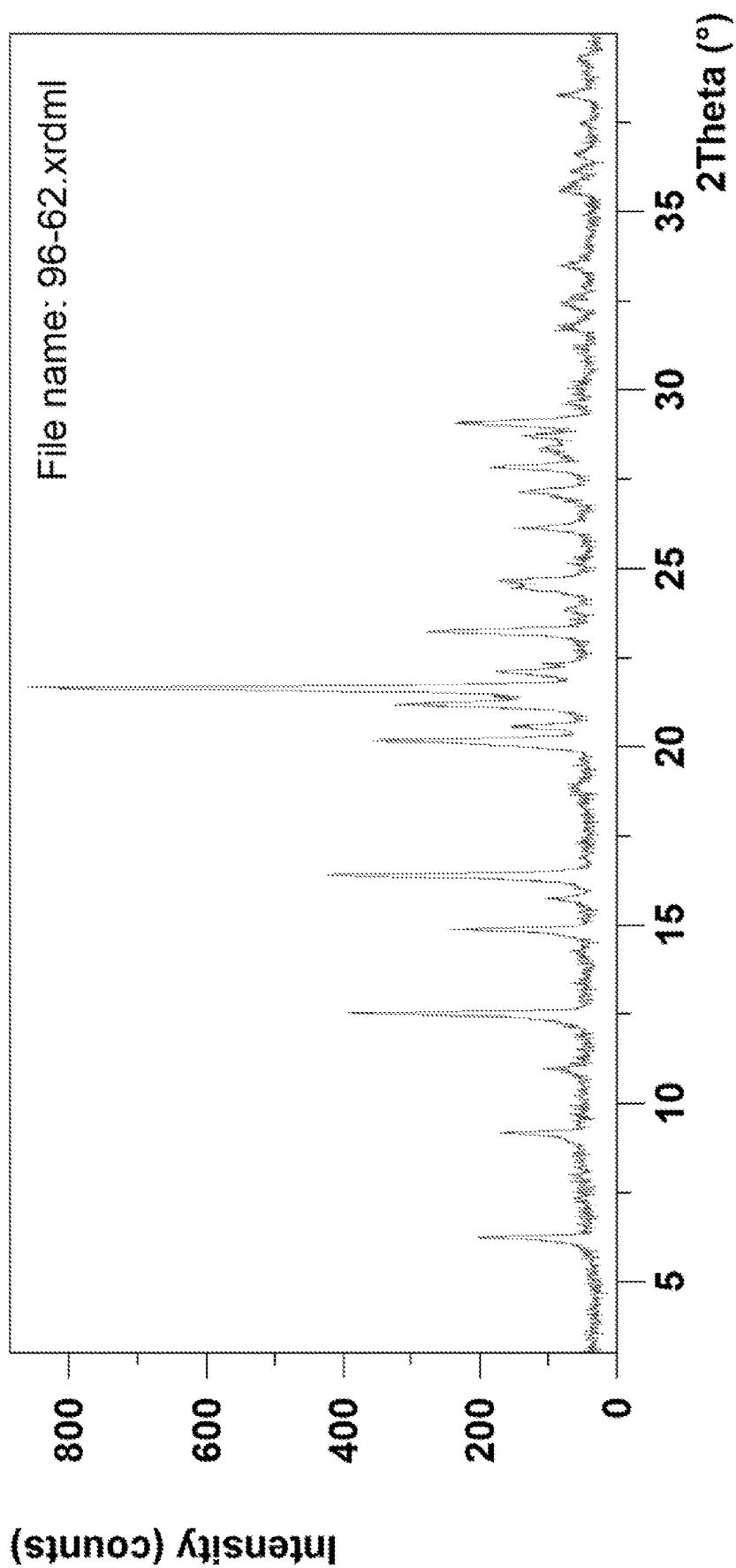
FIG. 22: X-Ray powder diffraction of example 7.
Figure 23:
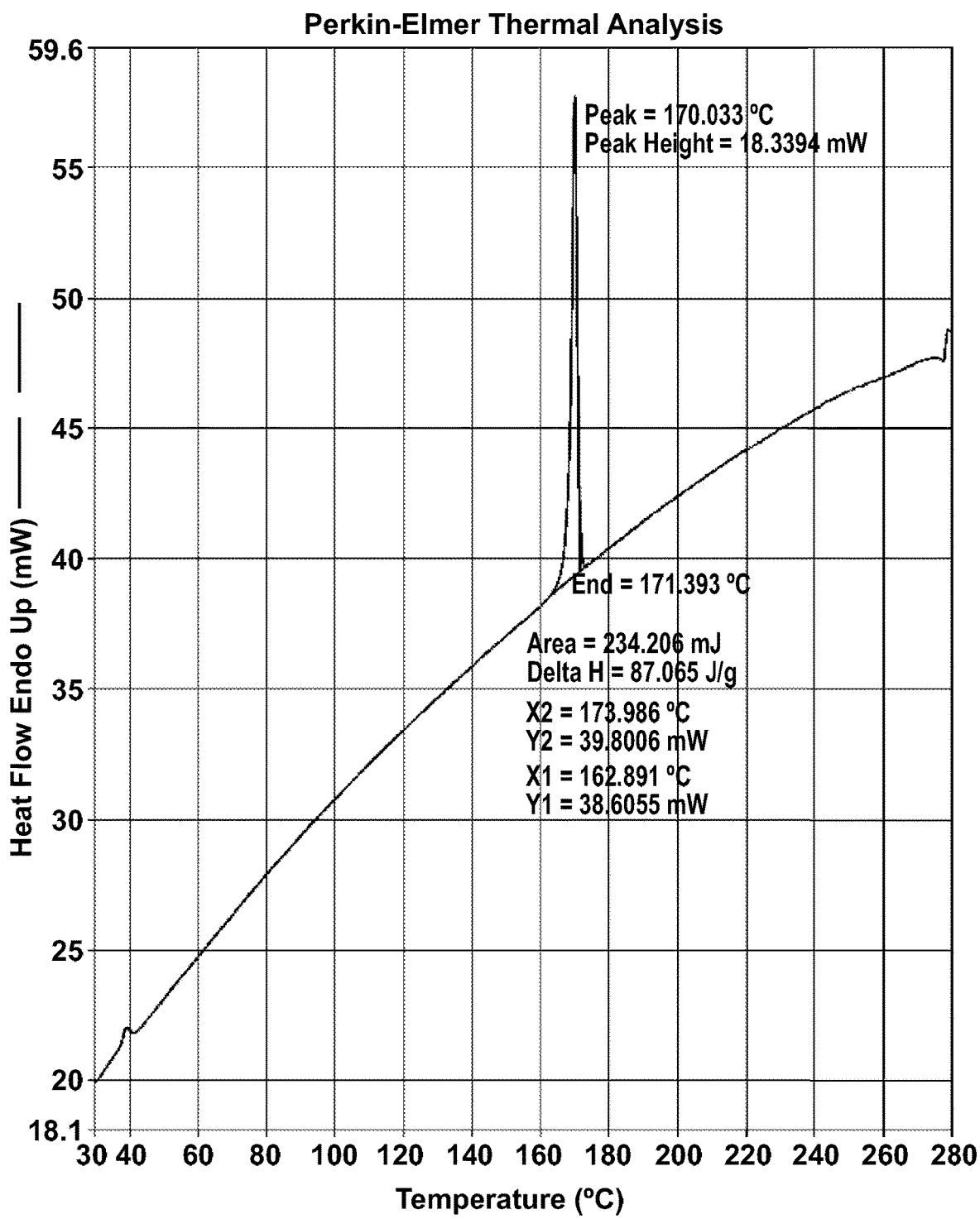
FIG. 23: Differential Scanning calorimetry (DSC) of example 7.
Figure 24:
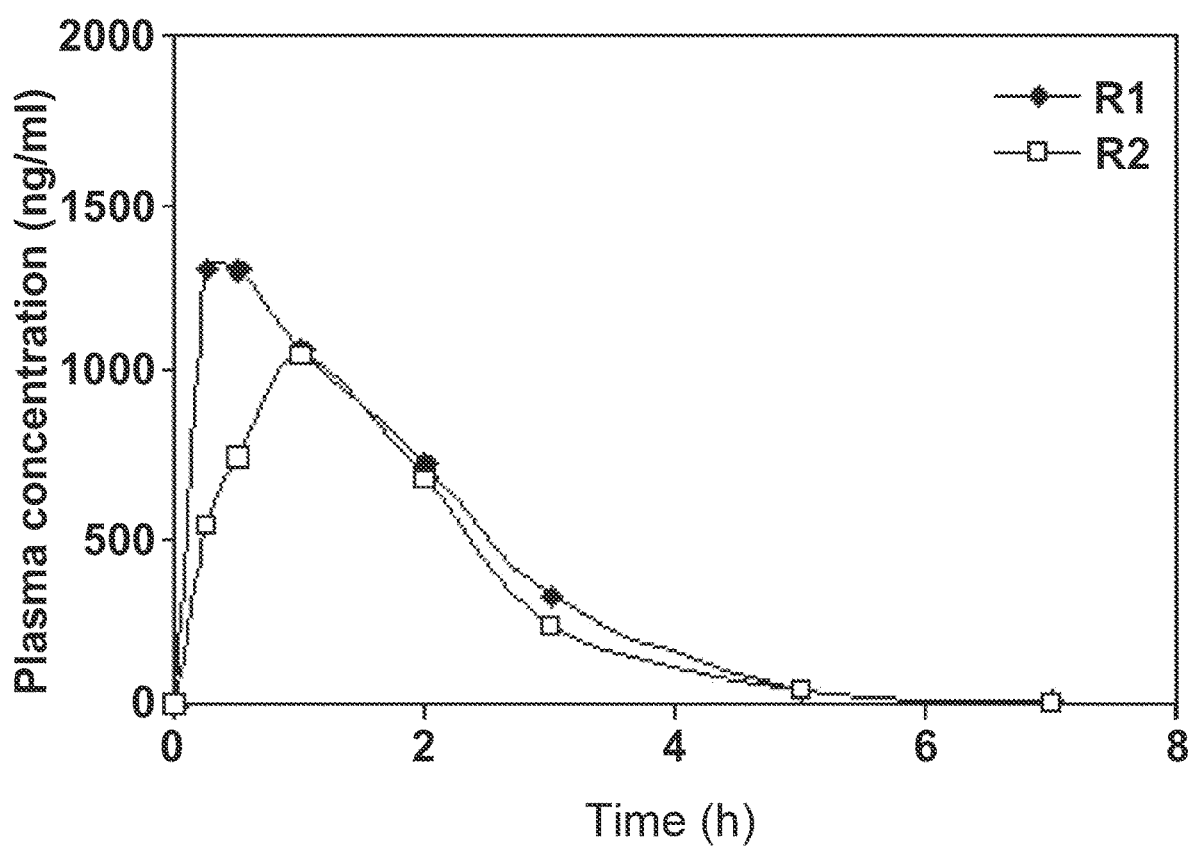
FIG. 24: Plasma concentration after oral administration of example 1.

Example 7 was additionally characterized characterized by X-Ray powder diffraction (FIG. 22) and by DSC (FIG. 23).

Alternatively, the compound of Example 7 can be prepared using the following procedure:

To an assay tube equipped with magnetic stirrer containing a solution of 1-acetyl-4-({[1-(3,4-difluorophenyl)-1H-pyrazol-3-yl]methoxy}ethyl)piperazine (47 mg, 0.129 mmol) in isobutyl methyl ketone (0.7 mL), a solution of HBr in isopropanol (140 µl of a solution prepared from 150 µl 48% HBr aqueous and 1.5 mL isopropanol, 0.13 mmol) was added at room temperature. After 3 h of stirring precipitation was not observed. Therefore the solution was seeded with the previous compound and a precipitate appeared. After 2 h of stirring at room temperature, the resultant suspension was filtered and washed with isobutyl methyl ketone (0.5 mL). After drying under vacuum at room temperature, the title compound was obtained as a crystalline solid (37 mg, 65% yield).

Example 8

Thermodynamic Solubility

General protocol for thermodynamic solubility at pH 7.4 and pH 2 are described.

A) Thermodynamic Solubility at pH 7.4
Buffer Solution
Phosphate buffer at pH 7.4 (25 mM) was prepared as follows:

A solution 25 mM of $Na_2HPO_4 \cdot 12H_2O$ (for 1 L of water, weight 8.96 g) was prepared A solution 25 mM de $KH_2PO_4$ (for 1 L of water weight 3.4 g) was prepared.

Disodium phosphate solution (812 mL) and potassium phosphate (182 mL) solution were mixed and pH checked to be 7.4.

Equipment
Precision analytical balance Mettler Toledo AT20.
Analytical balance Mettler Toledo PJ300.
Liquid chromatograph Waters Alliance 2695.
Stirrer Thermomixer Control of Eppendorf a 25° C. y 1250 rpm
pHmeter with combined semi-micro electrode.

Procedure
Test Substance
Around 4 mg of compound in an HPLC vial (by duplicate) was dissolved in 1 mL of buffer solution. After stirring in Thermomixer Comfort system for 24 hours at 25° C., in order to achieve thermodynamic equilibrium, solution was centrifuged at 3000 rpm for 15 minutes.

The resulting upper layer was collected with a glass pipette and transferred to the HPLC vials in order to inject them (10 μL) directly to the HPLC instrument.

Standards
Standards were made in methanol to ensure overall compound solubility. Preparation of standard calibrators is illustrated below:

Sol.A: 4 mg in 1 mL methanol (4000 μg/mL)
Sol.B: 0.5 mL Sol.A to 5 mL with methanol (400 μg/mL)
Sol.C: 1 mL Sol.B to 10 mL with methanol (40 μg/mL)
Sol.D: 5 mL Sol.0 to 50 mL with methanol (4 μg/mL)
Sol.E: 4 mL Sol.D to 10 mL with methanol (1.6 μg/mL)
Calibration curve was created through 10 μL injection of standards, beginning with the more diluted standard. Blanks were also injected, for checking the absence of contamination.

10 μl of test substance were injected, by duplicate, and the average peak area interpolated in the calibration curve (see Tables Examples below).

Chromatographic Conditions
Column: XBridge C18 (or similar) 2.5 μm 4.6×50 mm
Temperature: 35° C.
Mobile phase: ACN/ammonium bicarbonate 10 mM.
Gradient: 0-3.5 min: from 15% CAN to 95% CAN
   3.5-5 min: 95% ACN
   5-6 min: 95 a 15% ACN
   6-8 min: 15% ACN
Flow: 1.5 mL/min
Detection: around the maximum UV wavelength.

B) Thermodynamic Solubility at pH 2
The same previous procedure was performed with HCl 0.01N, instead of buffer solution.

8.1 Thermodinamical Solubility for Example 1
According to the described protocol Example 1 was completely dissolved so the solubility was higher than 4000 μg/mL (pH=7.4). (See Table 5 and Table 6).

TABLE 5

SAMPLES

| | Sample | Condition | Vial | RT | Date Acquired | Dilution | Inj.Vol. | Detection | Area | Height |
|---|---|---|---|---|---|---|---|---|---|---|
| 1 | Example 1 PROB pH 7.4 (1) | pH 7.4 | 44 | 2.2 | 21 Apr. 2012 6:01 | 1 | 10 | PDA 290.0 nm | 4351307 | 1096492 |
| 2 | Example 1 PROB pH 7.4 (1) | pH 7.4 | 44 | 2.2 | 21 Apr. 2012 6:10 | 1 | 10 | PDA 290.0 nm | 4230788 | 1078515 |
| 3 | Example 1 PROB pH 7.4 (2) | pH 7.4 | 45 | 2.2 | 21 Apr. 2012 6:19 | 1 | 10 | PDA 290.0 nm | 4757240 | 1203806 |
| 4 | Example 1 PROB pH 7.4 (2) | pH 7.4 | 45 | 2.2 | 21 Apr. 2012 6:28 | 1 | 10 | PDA 290.0 nm | 4804788 | 1214183 |

TABLE 6

| | Conc. | Units | Res Id | Cal Id | SampleWeight |
|---|---|---|---|---|---|
| 1 | 3928 | μg/ml | 13370 | 13347 | 1 |
| 2 | 3817.1 | μg/ml | 13371 | 13347 | 1 |
| 3 | 4301.5 | μg/ml | 13372 | 13347 | 1 |
| 4 | 4345.3 | μg/ml | 13373 | 13347 | 1 |
| Mean | 4097.976 | | | | |
| % RSD | 6.5 | | | | |

8.2 Thermodinamical Solubility for Example 2
According to the described protocol Example 2 was completely dissolved so the solubility was higher than 4000 μg/mL (pH=7.4). (See Table 7 and Table 8).

TABLE 7

SAMPLES

| | Sample | Condition | Vial | RT | Date Acquired | Dilution | Inj.Vol. | Detection | Area | Height |
|---|---|---|---|---|---|---|---|---|---|---|
| 1 | Example 1 PROB pH 7.4 (1) | pH 7.4 | 11 | 2.8 | 15 Apr. 2015 13:33 | 1 | 10 | PDA 290.0 nm | 4533277 | 1173198 |
| 2 | Example 1 PROB pH 7.4 (1) | pH 7.4 | 11 | 2.8 | 15 Apr. 2015 13:42 | 1 | 10 | PDA 290.0 nm | 4355437 | 1154617 |
| 3 | Example 1 PROB pH 7.4 (2) | pH 7.4 | 12 | 2.8 | 15 Apr. 2015 13:51 | 1 | 10 | PDA 290.0 nm | 4288239 | 1131879 |
| 4 | Example 1 PROB pH 7.4 (2) | pH 7.4 | 12 | 2.8 | 15 Apr. 2015 14:00 | 1 | 10 | PDA 290.0 nm | 4475398 | 1174356 |

TABLE 8

| | Conc. | Units | Res Id | Cal Id | Sample Weight |
|---|---|---|---|---|---|
| 1 | 4593.8 | μg/ml | 2800 | 2784 | 1 |
| 2 | 4408.7 | μg/ml | 2801 | 2784 | 1 |

TABLE 8-continued

|   | Conc. | Units | Res Id | Cal Id | Sample Weight |
|---|---|---|---|---|---|
| 3 | 4338.8 | µg/ml | 2802 | 2784 | 1 |
| 4 | 4533.6 | µg/ml | 2803 | 2784 | 1 |
| Mean | 4468.706 | | | | |
| % RSD | 2.6 | | | | |

Example 9

Pharmacokinetic Parameters Cmax and AUC

The pharmacokinetics of Example 1 and 2 were tested using the following protocol:

Animals

Male Wistar rats weighing 250 to 300 g (±20) supplied by Harlan were used. Water and food was available ad libitum throughout the study.

Materials

|   | Supplier | Reference |
|---|---|---|
| (Hydroxypropyl)methylcellulose | Sigma-Aldrich | H9262 |
| Physiological serum Vitulia (isotonic) | ERN | 999789.2 |
| Fluorane - isoflurane | Abbot | 880393H0 |
| Ethanol | Sharlau | ET0010 |
| Anhydrous dimethylsulphoxide (DMSO) | Carlo Erba | 445131 |
| Acetonitrile | Sigma-Aldrich | 34967 |
| Formic acid (98-100% purity) | Riedel de Haen | 33015 |
| Heparinized tubes (Microvette ®) | Sarstedt | CB300 |

Administration and Sample Collection

Two rats (R1 and R2) were used in the pharmacokinetic oral studies.

A single dose of tested compound was administered by oral gavage [10 mg/kg as free base (Example 0)] in 0.5% hydroxypropyl methylcellulose (1 mg/ml). From each rat, serial blood samples were collected at 15 and 30 min, 1, 2, 3, 5, 7 and 24 h.

Blood was collected from the saphenous veins into heparinized tubes. Plasma was obtained by blood centrifugation at 4° C. and 2280×g for 10 min and kept at −80° C. until analysis.

Sample Processing

Tested compound concentration in plasma samples was determined by least-squares linear regression using a ten-point calibration curve. The calibration curve was prepared in blank plasma from a working solution of 1 mg/ml in DMSO.

Samples were thawed at room temperature on the day of analysis. After plasma protein precipitation of samples and calibration standards with acetonitrile (1:4.3; v/v), the mixture was vortexed and centrifuged (4° C. and 16090×g for 10 min). Finally, an aliquot of the resultant supernatant was diluted 1/10 with water (0.1% formic acid) before analysis.

Analytical Method

Tested compound plasma concentrations were determined by high performance liquid chromatography-triple quadrupole mass spectrometry (HPLC-MS/MS) through the following method:

Column: Atlantis® T3 column (2.1×100 mm, 3 µm) (Waters).

Mobile phase: A: 0.0155% Formic water

B: 0.0155% Formic Acetonitrile

Autosampler wash: Solvent 1:Acetonitrile

Solvent 2: 5% Acetonitrile+95% Water

Pharmacokinetic Analysis

Standard pharmacokinetic parameters, such as area under the curve (AUC), peak plasma concentration ($C_{max}$), time to peak concentration ($t_{max}$), oral bioavailability (F), total plasma clearance (Cl), volume of distribution at steady-state (Vss), mean residence time (MRT) and terminal half-life ($t_{1/2}$), were determined by non-compartmental analysis of the plasma concentration-time curves (Phoenix v. 6.2.1.51, Pharsight, C A).

9.1 Pharmacokinetic Parameters for Example 1

TABLE 9

Figure 25:
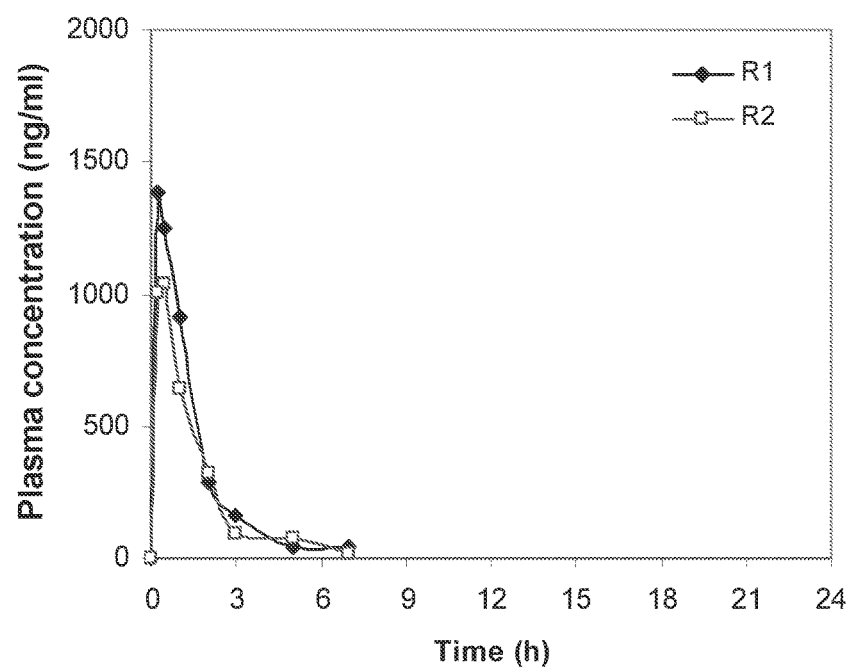
FIG. 25: Plasma concentration after oral administration of example 2.

Plasma concentration after single oral administration of 10 mg/kg to male Wistar rat (FIG. 25)

| time | Plasma concentration (ng/ml) | |
|---|---|---|
| (h) | R1 | R2 |
| 24 | <lloq | <lloq |
| 7 | 12.8 | 11.5 |
| 5 | 49.6 | 46.9 |
| 3 | 323.1 | 233.1 |
| 2 | 722.8 | 673.9 |
| 1 | 1066.8 | 1045.9 |
| 0.5 | 1301.9 | 741.6 |
| 0.25 | 1310.9 | 534.9 |

LLOQ: 2 ng/ml

TABLE 10

Pharmacokinetic parameters after single oral administration of 10 mg/kg to male Wistar rat

| Animal | $t_{1/2}$ (h) | $C_{max}$ (ng/ml) | $t_{max}$ (h) | AUC (ng · h/ml) | F (%)[a] |
|---|---|---|---|---|---|
| 1 | 0.9 | 1311 | 0.25 | 2950 | 66 |
| 2 | 0.9 | 1046 | 1.00 | 2340 | 53 |
| Mean | 0.9 | 1178 | 0.63 | 2645 | 60 |
| SD | 0.0 | 187 | 0.53 | 432 | 9 |

[a]Mean AUC after i.v. administration was used for F calculation

Thus it can be concluded that:

After oral administration to rat of 10 mg/kg, Example 1 achieves a peak plasma concentration of approximately 1000 ng/ml at 0.6 h post-administration (Table 9) and shows a good oral bioavailability (60%) (Table 10).

The terminal half-life is very short (<1 h). This terminal half-life is related to a high plasma clearance (70% liver blood flow).

Example 1 shows a volume of distribution higher than the total body water volume (1.2 vs. 0.6 l/kg). This result suggests that Example 1 is able to cross cellular membranes and/or has affinity for tissue components.

When the volume of distribution is higher than total body water it is considered the compound is widely distributed and a good therapeutic target exposure could be expected.

9.2 Pharmacokinetic Parameters for Example 2

TABLE 11

Plasma concentration after single oral administration of 10 mg/kg to male Wistar rat (FIG. 26)

| time | Plasma concentration (ng/ml) | |
|---|---|---|
| (h) | R1 | R2 |
| 24 | <lloq | <lloq |
| 7 | 41 | 13 |

TABLE 11-continued

Plasma concentration after single oral administration of 10 mg/kg to male Wistar rat (FIG. 26)

| time (h) | Plasma concentration (ng/ml) | |
| --- | --- | --- |
|  | R1 | R2 |
| 5 | 45 | 75 |
| 3 | 157 | 95 |
| 2 | 289 | 317 |
| 1 | 907 | 639 |
| 0.5 | 1251 | 1039 |
| 0.25 | 1386 | 1002 |

Lloq: 2 ng/ml

TABLE 12

Pharmacokinetic parameters after single oral administration of 10 mg/kg to male Wistar rat

| Animal | $t_{1/2}$ (h) | $C_{max}$ (ng/ml) | $t_{max}$ (h) | AUC (ng · h/ml) | F (%)[a] |
| --- | --- | --- | --- | --- | --- |
| 1 | 1.7 | 1386 | 0.25 | 2227 | 50 |
| 2 | 1.2 | 1039 | 0.50 | 1768 | 40 |
| Mean | 1.5 | 1213 | 0.38 | 1997 | 45 |
| SD | 0.3 | 246 | 0.18 | 325 | 7 |

[a]Mean AUC after i.v. administration was used for F calculation

Thus it can be concluded that:

After oral administration to rat of 10 mg/kg, Example 2 achieves a peak plasma concentration of approximately 1213 ng/ml at 0.4 h post-administration (Table 11).

The terminal half-life is moderate (1.5 h) (Table 12).

The peak plasma concentration is achieved at 0.63 (example 1) and 0.38 h post-administration (example 2) suggesting a fast absorption and therefore, a fast onset of action could be expected.

High exposure is preferred to assure the desired activity for the compound. After 10 mg/kg administration, the area under the curve (AUC) gives an oral exposure around 2600 (example 1) and 2000 ng·h/ml (example 2), values that could be considered high enough.

Bioavailability (F) is the fraction of the dose that reaches systemic circulation unchanged. The good value found (60% for example 1 and 45% for example 2) is considered to provoke an exposure high enough and also valid for avoiding the risk of high patient-to-patient variability of blood concentrations of a compound with low bioavailability.

The invention claimed is:

1. A crystalline salt of 1-(4-(2-((1-(3,4-difluorophenyl)-1H-pyrazol-3-yl)methoxy)ethyl)piperazin-1-yl)ethanone, wherein said salt is selected from hydrochloride, maleate, fumarate, succinate, oxalate and/or hydrobromide.

2. The crystalline salt according to claim 1 wherein the salt is the hydrochloride salt of 1-(4-(2-((1-(3,4-difluorophenyl)-1H-pyrazol-3-yl)methoxy)ethyl)piperazin-1-yl)ethanone.

3. The crystalline salt according to claim 1 wherein the salt is the maleate salt of 1-(4-(2-((1-(3,4-difluorophenyl)-1H-pyrazol-3-yl)methoxy)ethyl)piperazin-1-yl)ethanone.

4. A pharmaceutical composition comprising at least a crystalline salt according to claim 1.

5. A method for the manufacture of a medicament comprising combining the crystalline salt as defined in claim 1 with a pharmaceutically acceptable excipient.

* * * * *